(12) United States Patent
Al-Ali et al.

(10) Patent No.: US 11,813,036 B2
(45) Date of Patent: Nov. 14, 2023

(54) MEDICAL MONITORING DEVICE HAVING MULTIPLE CONFIGURATIONS

(71) Applicant: MASIMO CORPORATION, Irvine, CA (US)

(72) Inventors: Ammar Al-Ali, San Juan Capistrano, CA (US); Nicholas Evan Barker, Laguna Beach, CA (US); Steven Egge, Laguna Hills, CA (US); Chad A. DeJong, Los Angeles, CA (US); Sujin Hwang, Irvine, CA (US); Massi Joe E. Kiani, Laguna Niguel, CA (US); Bilal Muhsin, San Clemente, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 17/168,764

(22) Filed: Feb. 5, 2021

(65) Prior Publication Data

US 2021/0330188 A1    Oct. 28, 2021

Related U.S. Application Data

(63) Continuation of application No. 15/962,477, filed on Apr. 25, 2018, now Pat. No. 10,918,281.
(Continued)

(51) Int. Cl.
*H05K 5/00* (2006.01)
*A61B 5/00* (2006.01)
(Continued)

(52) U.S. Cl.
CPC .............. *A61B 5/0022* (2013.01); *A61B 5/02* (2013.01); *A61B 5/0205* (2013.01);
(Continued)

(58) Field of Classification Search
CPC ........................................................ G06F 1/16
See application file for complete search history.

(56) References Cited

U.S. PATENT DOCUMENTS

| 3,209,988 A | 10/1965 | Fox |
| 3,980,075 A | 9/1976 | Heule |

(Continued)

OTHER PUBLICATIONS

Addison et al., "Increasing Signal Processing Sophistication in the Calculation of the Respiratory Modulation of the Photoplethysmogram (DROP)", Journal of Clinical Monitoring and Computing, 2015, vol. 29, pp. 363-372.

(Continued)

*Primary Examiner* — Jerry Wu
(74) *Attorney, Agent, or Firm* — Knobbe, Martens, Olson & Bear, LLP

(57) ABSTRACT

A patient monitoring device can be configured to provide fast and reliable physiological measurements in a variety of care settings including at a patient's home. The device can include a compact, standalone monitor with telehealth capabilities as well as an intuitive interface for use at home. The device can include a blood pressure, capnography, or pulse oximetry module. A device can include a sleek and continuous outer surface that is easy to clean and generally free of crevices, holes, or surfaces that collect external contaminants. For example, portions of the housing can connect together using a limited number of screws, thereby limiting a number of holes. The device can include a vent cover that can be rotated to reconfigure the function of the vent cover. For example, the vent cover can function as a stabilization feature and/or a cover for a ventilation hole, while permitting exhaust through the ventilation hole.

14 Claims, 20 Drawing Sheets

Related U.S. Application Data

(60) Provisional application No. 62/526,182, filed on Jun. 28, 2017, provisional application No. 62/492,108, filed on Apr. 28, 2017, provisional application No. 62/490,398, filed on Apr. 26, 2017.

(51) Int. Cl.
*A61B 5/02* (2006.01)
*A61B 5/0205* (2006.01)
*G16H 40/60* (2018.01)
*A61B 5/145* (2006.01)
*G16H 40/67* (2018.01)
*G16H 40/63* (2018.01)

(52) U.S. Cl.
CPC ........ *A61B 5/7445* (2013.01); *A61B 5/14542* (2013.01); *A61B 2560/0443* (2013.01); *G16H 40/60* (2018.01); *G16H 40/63* (2018.01); *G16H 40/67* (2018.01)

(56) References Cited

U.S. PATENT DOCUMENTS

| | | |
|---|---|---|
| 4,114,604 A | 9/1978 | Shaw et al. |
| 4,796,634 A | 1/1989 | Huntsman et al. |
| 4,960,128 A | 10/1990 | Gordon et al. |
| 4,964,408 A | 10/1990 | Hink et al. |
| 5,041,187 A | 8/1991 | Hink et al. |
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,836,884 A | 11/1998 | Chio |
| 5,845,643 A | 12/1998 | Vergano et al. |
| 5,860,919 A | 1/1999 | Kiani-Azarbayjany et al. |
| 5,862,805 A | 1/1999 | Nitzan |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,120,459 A | 9/2000 | Nitzan et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |

(56) References Cited

U.S. PATENT DOCUMENTS

| | | |
|---|---|---|
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,179,228 B2 | 2/2007 | Banet |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |

(56) References Cited

U.S. PATENT DOCUMENTS

| | | |
|---|---|---|
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| D643,126 S | 8/2011 | Barker et al. |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |

(56) References Cited

U.S. PATENT DOCUMENTS

| | | | |
|---|---|---|---|
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |

(56) References Cited

U.S. PATENT DOCUMENTS

| | | |
|---|---|---|
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,924,897 B1 | 3/2018 | Abdul-Hafiz |
| 9,936,917 B2 | 4/2018 | Poeze et al. |
| 9,955,937 B2 | 5/2018 | Telfort |
| 9,965,946 B2 | 5/2018 | Al-Ali et al. |
| D820,865 S | 6/2018 | Muhsin et al. |
| 9,986,952 B2 | 6/2018 | Dalvi et al. |
| D822,215 S | 7/2018 | Al-Ali et al. |
| D822,216 S | 7/2018 | Barker et al. |
| 10,010,276 B2 | 7/2018 | Al-Ali et al. |
| 10,086,138 B1 | 10/2018 | Novak, Jr. |
| 10,111,591 B2 * | 10/2018 | Dyell .................. A61B 5/7475 |
| D833,624 S | 11/2018 | DeJong et al. |
| 10,123,729 B2 | 11/2018 | Dyell et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,205,291 B2 | 2/2019 | Scruggs et al. |
| 10,226,187 B2 | 3/2019 | Al-Ali et al. |
| 10,231,657 B2 | 3/2019 | Al-Ali et al. |
| 10,231,670 B2 | 3/2019 | Blank et al. |
| RE47,353 E | 4/2019 | Kiani et al. |
| 10,279,247 B2 | 5/2019 | Kiani |
| 10,292,664 B2 | 5/2019 | Al-Ali |
| 10,299,720 B2 | 5/2019 | Brown et al. |
| 10,327,337 B2 | 6/2019 | Schmidt et al. |
| 10,327,713 B2 | 6/2019 | Barker et al. |
| 10,332,630 B2 | 6/2019 | Al-Ali |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D886,849 S | 6/2020 | Muhsin et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf |
| D906,970 S | 1/2021 | Forrest et al. |
| D908,213 S | 1/2021 | Abdul-Hafiz et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |

(56) References Cited

U.S. PATENT DOCUMENTS

| | | |
|---|---|---|
| D917,046 S | 4/2021 | Abdul-Hafiz et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| D933,233 S | 10/2021 | Al-Ali et al. |
| D933,234 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D950,738 S | 5/2022 | Al-Ali et al. |
| D957,648 S | 7/2022 | Al-Ali |
| 11,382,567 B2 | 7/2022 | O'Brien et al. |
| 11,389,093 B2 | 7/2022 | Triman et al. |
| 11,406,286 B2 | 8/2022 | Al-Ali et al. |
| 11,417,426 B2 | 8/2022 | Muhsin et al. |
| 11,439,329 B2 | 9/2022 | Lamego |
| 11,445,948 B2 | 9/2022 | Scruggs et al. |
| D965,789 S | 10/2022 | Al-Ali et al. |
| D967,433 S | 10/2022 | Al-Ali et al. |
| 11,464,410 B2 | 10/2022 | Muhsin |
| 11,504,058 B1 | 11/2022 | Sharma et al. |
| 11,504,066 B1 | 11/2022 | Dalvi et al. |
| D971,933 S | 12/2022 | Ahmed |
| D973,072 S | 12/2022 | Ahmed |
| D973,685 S | 12/2022 | Ahmed |
| D973,686 S | 12/2022 | Ahmed |
| D974,193 S | 1/2023 | Forrest et al. |
| D979,516 S | 2/2023 | Al-Ali et al. |
| D980,091 S | 3/2023 | Forrest et al. |
| 11,596,363 B2 | 3/2023 | Lamego |
| 11,627,919 B2 | 4/2023 | Kiani et al. |
| 11,637,437 B2 | 4/2023 | Al-Ali et al. |
| D985,498 S | 5/2023 | Al-Ali et al. |
| 11,653,862 B2 | 5/2023 | Dalvi et al. |
| D989,112 S | 6/2023 | Muhsin et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0167010 A1 | 9/2003 | Pinsky |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2006/0224070 A1 | 10/2006 | Sharrock et al. |
| 2007/0041157 A1* | 2/2007 | Wang ............... G06F 1/203 361/679.48 |
| 2007/0073116 A1 | 3/2007 | Kiani et al. |
| 2007/0179386 A1 | 8/2007 | Michard et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0198140 A1 | 8/2009 | Riobo Aboy et al. |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0054267 A1 | 3/2011 | Fidacaro et al. |
| 2011/0082711 A1 | 4/2011 | Poeze et al. |
| 2011/0087081 A1 | 4/2011 | Kiani et al. |
| 2011/0105854 A1 | 5/2011 | Kiani et al. |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2012/0319816 A1 | 12/2012 | Al-Ali |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0317378 A1 | 11/2013 | Krivitski et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0081175 A1 | 3/2014 | Telfort |
| 2014/0094664 A1 | 4/2014 | Sola I Caros et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0135588 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |

(56) References Cited

U.S. PATENT DOCUMENTS

| | | |
|---|---|---|
| 2014/0276115 A1 | 9/2014 | Dalvi et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0316278 A1 | 10/2014 | Addison et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080669 A1 | 3/2015 | Settels et al. |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Muhsin et al. |
| 2015/0099950 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0165312 A1 | 6/2015 | Kiani |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2016/0029932 A1 | 2/2016 | Al-Ali |
| 2016/0055740 A1 | 2/2016 | Fuchs |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0143548 A1 | 5/2016 | Al-Ali |
| 2016/0148531 A1 | 5/2016 | Bleich et al. |
| 2016/0166182 A1 | 6/2016 | Al-Ali et al. |
| 2016/0166183 A1 | 6/2016 | Poeze et al. |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0027456 A1 | 2/2017 | Kinast et al. |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0202490 A1 | 7/2017 | Al-Ali et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali |
| 2017/0340293 A1 | 11/2017 | Al-Ali et al. |
| 2017/0360310 A1 | 12/2017 | Kiani |
| 2017/0367632 A1 | 12/2017 | Al-Ali et al. |
| 2018/0008146 A1 | 1/2018 | Al-Ali et al. |
| 2018/0014752 A1 | 1/2018 | Al-Ali et al. |
| 2018/0028124 A1 | 2/2018 | Al-Ali et al. |
| 2018/0103874 A1 | 4/2018 | Lee et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0256087 A1 | 9/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2019/0015023 A1 | 1/2019 | Monfre |
| 2019/0117070 A1 | 4/2019 | Muhsin et al. |
| 2019/0200941 A1 | 7/2019 | Chandran et al. |
| 2019/0239787 A1 | 8/2019 | Pauley et al. |
| 2019/0320906 A1 | 10/2019 | Olsen |
| 2019/0374139 A1 | 12/2019 | Kiani et al. |
| 2019/0374173 A1 | 12/2019 | Kiani et al. |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |

(56) References Cited

U.S. PATENT DOCUMENTS

| | | |
|---|---|---|
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0151521 A1 | 5/2022 | Krishnamani et al. |
| 2022/0218244 A1 | 7/2022 | Kiani et al. |
| 2022/0287574 A1 | 9/2022 | Telfort et al. |
| 2022/0296161 A1 | 9/2022 | Al-Ali et al. |
| 2022/0361819 A1 | 11/2022 | Al-Ali et al. |
| 2022/0379059 A1 | 12/2022 | Yu et al. |
| 2022/0392610 A1 | 12/2022 | Kiani et al. |
| 2023/0028745 A1 | 1/2023 | Al-Ali |
| 2023/0038389 A1 | 2/2023 | Vo |
| 2023/0045647 A1 | 2/2023 | Vo |
| 2023/0058052 A1 | 2/2023 | Al-Ali |
| 2023/0058342 A1 | 2/2023 | Kiani |
| 2023/0069789 A1 | 3/2023 | Koo et al. |
| 2023/0087671 A1 | 3/2023 | Telfort et al. |
| 2023/0110152 A1 | 4/2023 | Forrest et al. |
| 2023/0111198 A1 | 4/2023 | Yu et al. |
| 2023/0115397 A1 | 4/2023 | Vo et al. |
| 2023/0116371 A1 | 4/2023 | Mills et al. |
| 2023/0135297 A1 | 5/2023 | Kiani et al. |
| 2023/0138098 A1 | 5/2023 | Telfort et al. |
| 2023/0145155 A1 | 5/2023 | Krishnamani et al. |
| 2023/0147750 A1 | 5/2023 | Barker et al. |

OTHER PUBLICATIONS

Chandler et al., "Pulse Oximeter Plethysmograph Variation and its Relationship to the Arterial Waveform in Mechanically Ventilated Children", Journal of Clinical Monitoring and Computing, Mar. 10, 2012, pp. 1-7.

Kim, et al., Pulse pressure variation and stroke vol. variation to predict fluid responsiveness in patients undergoing carotid endarterectomy, Korean Journal Anesthesiology, Sep. 2013, vol. 65, No. 3, pp. 237-243.

Lee, et al., Multivariate Classification of Systemic Vascular Resistance Using Photoplethysmography, Physiological Measurement, vol. 32 (2011) pp. 1117-1132.

"Subsequent", Merriam-Webster Dictionary, Web, Nov. 5, 2019, 1 page.

Sun, et al., Estimating Cardiac Output from Arterial Blood Pressure Waveforms: a Critical Evaluation Using the MIMIC II Database, Harvard-MIT Division of Health Sciences and Technology, MIT, Cambridge, MA, in 4 pages.

Letter from M G Willehemen to Masimo Corporation re 510(k) No. K170168, U.S. Food & Drug Administration, dated Sep. 14, 2017 in 14 pages.

Letter from Michael J. Ryan to Masimo Corporation re 510(k) No. K180046, U.S. Food & Drug Administration, dated Oct. 23, 2018 in 13 pages.

Letter from Todd D. Courtney to Masimo Corporation re 510(k) No. K183697, U.S. Food & Drug Administration, dated May 15, 2019 in 14 pages.

Letter from Ka N. To to Masimo Corporation re 510(k) No. K191059, U.S. Food & Drug Administration, dated Dec. 27, 2019 in 12 pages.

Letter from James J. Lee to Masimo Corporation re 510(k) No. K193242, U.S. Food & Drug Administration, dated Feb. 27, 2020 in 21 pages.

Letter from Todd D. Courtney to Masimo Corporation re 510(k) No. K193626, U.S. Food & Drug Administration, dated Aug. 10, 2020 in 11 pages.

\* cited by examiner

MEDICAL MONITORING DEVICE HAVING MULTIPLE CONFIGURATIONS

RELATED APPLICATIONS

The present application is a continuation of U.S. application Ser. No. 15/962,477, filed Apr. 25, 2018, entitle "MEDICAL MONITORING DEVICE HAVING MULTIPLE CONFIGURATIONS," which claims priority to U.S. Provisional Application No. 62/490,398, filed Apr. 26, 2017, entitled "MEDICAL MONITORING COMPONENT FOR STABILITY AND VENTILATION," U.S. Provisional Application No. 62/492,108, filed Apr. 28, 2017, entitled "MEDICAL MONITORING DEVICE HAVING MULTIPLE CONFIGURATIONS," and U.S. Provisional Application No. 62/526,182, filed Jun. 28, 2017, entitled "MEDICAL MONITORING DEVICE HAVING MULTIPLE CONFIGURATIONS," each of which is hereby incorporated by reference in its entirety.

TECHNICAL FIELD

The present disclosure relates generally to the field of patient monitoring devices. In particular, the present disclosure relates to a patient monitor having multiple configurations configured to provide a plurality of physiological measuring capabilities based at least in part on the configuration. In addition, the present disclosure relates to a vent cover for a patient monitoring device, the vent cover configured to protect a ventilation hole from external contaminants and/or provide a stabilization feature for the patient monitoring device.

BACKGROUND

Telemedicine facilitates provide efficient and coordinated care, making homestay a possibility for a variety of patients. Remote monitoring and surveillance, along with virtual consultations, can reduce hospital admissions and length of stay, cutting costs while reinforcing continued routine care and self-management. However, limited integrated communication capabilities, lack of device interoperability, and poor network connectivity have hindered the rapid adoption of telemedicine solutions.

SUMMARY

The present disclosure provides for improved monitoring of patients through the use of a compact, standalone monitor for use at home. A patient monitoring device can include a housing configured to house a display. The housing can define a recess and can further define one or more ventilation holes within the recess. The one or more ventilation holes can allow air to flow through the housing of the patient monitoring device. The device can further include a vent cover coupled to the housing and configured to be positioned in one of a plurality of configurations. Rotation of the vent cover can transition the vent cover between configurations.

The device of the preceding paragraph may also include any combination of the following features described in this paragraph, among others described herein. The plurality of configurations can include one or more of a first configuration and/or a second configuration. The first configuration can include the vent cover oriented within the recess to at least partially cover the one or more ventilation holes to protect the one or more ventilation holes from at least some external contaminants. While in the first configuration, the vent cover may or may not completely block the ventilation holes, but will continue to permit the air to flow through the housing of the patient monitoring device through the one or more ventilation holes. The second configuration can include the vent cover oriented to provide a stabilization feature to the patient monitoring device. While in the first configuration, the orientation of the vent cover may or may not completely block the ventilation holes, but will continue to permit the air to flow through the housing of the patient monitoring device through the one or more ventilation holes.

The device of any of the preceding paragraphs may also include any combination of the following features described in this paragraph, among others described herein. While in the first configuration, at least a portion of an outer surface of the vent cover can be level, even, or flush with at least a portion of an outer surface of the housing. The recess can include first indentations and second indentations. While in the first configuration, the vent cover can reside in the first indentations. While in the second configuration, the vent cover can reside in the second indentations. The first indentations can be perpendicular to the second indentations. The housing can further define one or more raised indentations to provide a barrier between the first indentations and the second indentations.

The device of any of the preceding paragraphs may also include any combination of the following features described in this paragraph, among others described herein. While in the second configuration, the stabilization feature can provide lateral support to the patient monitoring device. While in the second configuration, the vent cover can be oriented such that its ends protrude past edges of the housing. The device can further include a locking mechanism configured to limit rotation of the vent cover. The vent cover can further include a body, an engagement member, and an extension member. The extension member can extend between the body and the engagement member. The vent cover can be configured to rotate about an axis corresponding to the extension member. The first configuration and the second configuration can be separated by 45, 90, 135, or 180 degrees of rotation of the vent cover.

The device of any of the preceding paragraphs may also include any combination of the following features described in this paragraph, among others described herein. The housing can be configured to house at least one of a non-invasive blood pressure module, a capnography module, or a pulse oximetry module. The housing can include a plurality of housing portions configured to mate via a plurality of connection features to attach the housing portions together. The plurality of connection features can include one or more of t-shaped connection features and/or snap connection features. The t-shaped connection features can include a t-shaped protrusion and a t-shaped aperture configured to mate with the t-shaped protrusion.

The present disclosure also provides for an improved method of configuring a vent cover of a patient monitoring device. This can include providing a housing that defines a recess and further defines one or more ventilation holes within the recess. The one or more ventilation holes can allow air to flow through the housing of the patient monitoring device. The method can further include providing a vent cover coupled to the housing and oriented within the recess to at least partially cover the one or more ventilation holes to protect the one or more ventilation holes from at least some external contaminants. In some cases, this orientation is referred to as the first configuration or a storage configuration. While in the first configuration, the vent cover does not completely block the ventilation holes, but continues to permit the air to flow through the housing of the patient monitoring device through the one or more ventilation holes. The method can further include rotating the vent cover, which reorients the vent cover for use as a stabilization feature to provide lateral support to the patient monitoring device. In some cases, this is referred to as the second or a stabilizing configuration. Each of the orientations or configurations of the vent cover (for example, first configuration, second configuration, or an intermediate configuration) permit the air to flow through the housing of the patient monitoring device through the one or more ventilation holes.

The method of the preceding paragraph may also include any combination of the following features or steps described in this paragraph, among others described herein. Rotating the vent cover can include rotating the vent cover 45, 90, 135, or 180 degrees about an axis of the vent cover. The housing can be configured to house at least one of a non-invasive blood pressure module, a capnography module, or a pulse oximetry module.

The present disclosure also provides for an improved method of configuring a vent cover of a patient monitoring device. This can include providing a housing that defines a recess and further defines one or more ventilation holes within the recess. The one or more ventilation holes can allow air to flow through the housing of the patient monitoring device. The method can further include providing a vent cover coupled to the housing and oriented to provide a stabilization feature that can provide lateral support to the patient monitoring device. In some cases, this orientation is referred to as the second configuration or a stabilizing configuration. While in the second configuration, the vent cover does not completely block the ventilation holes, but continues to permit the air to flow through the housing of the patient monitoring device through the one or more ventilation holes. The method can further include rotating the vent cover, which reorients the vent cover within the recess to at least partially cover the one or more ventilation holes to protect the one or more ventilation holes from at least some external contaminants. In some cases, this is referred to as the first configuration or a storage configuration. Each of the orientations or configurations of the vent cover (for example, first configuration, second configuration, or an intermediate configuration) permit the air to flow through the housing of the patient monitoring device through the one or more ventilation holes.

The method of the preceding paragraph may also include any combination of the following features or steps described in this paragraph, among others described herein. Rotating the vent cover can include rotating the vent cover 45, 90, 135, or 180 degrees about an axis of the vent cover. The housing can be configured to house at least one of a non-invasive blood pressure module, a capnography module, or a pulse oximetry module.

The present disclosure also provides for an improved patient monitoring device. A patient monitoring device can be configured to provide videoconferencing capabilities, which can provide more efficient and coordinated care, making homestay a possibility for a variety of patients. Remote monitoring and surveillance, along with virtual consultations, can reduce hospital admissions and length of stay, cutting costs while reinforcing continued routine care and self-management. The patient monitoring device can be capable of gathering patient data from a variety of devices and transmitting data to remote locations and/or electronic medical records (EMRs). The patient monitoring device can include one or more built-in cameras to facilitate one- and two-way patient-physician communication.

The present disclosure also provides for an improved patient monitoring device. The patient monitoring device can include a sleek and continuous outer surface that is easy to clean and generally free of crevices, holes, or surfaces that collect external contaminants. The housing of the patient monitoring device can include multiple housing portions that are configured to attach using internal connection features, while using limited or no screws or screw holes. The housing of the patient monitoring device can connect with display using similar internal connection features and using limited or no screws or screw holes. By limiting a number of screw holes, the housing has fewer crevices, thereby reducing the amount of dirt or other contaminants that are stuck in the housing.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

BRIEF DESCRIPTION OF THE DRAWINGS

The following drawings and the associated descriptions are provided to illustrate embodiments of the present disclosure and do not limit the scope of the claims.

Figure 1:
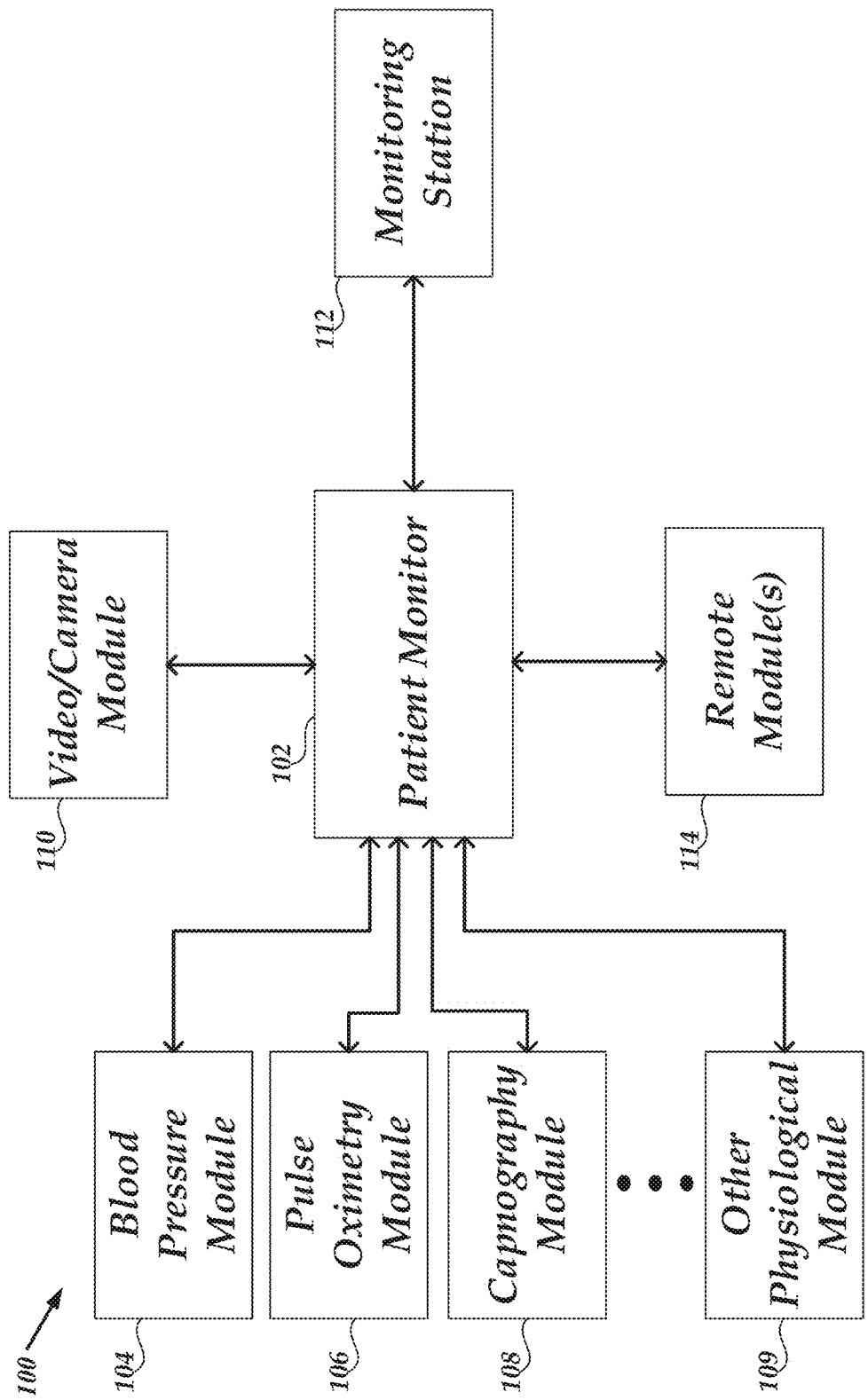
FIG. 1 illustrates a schematic block diagram of an example patient monitoring system.

While the foregoing "Brief Description of the Drawings" references generally various embodiments of the disclosure, an artisan will recognize from the disclosure herein that such embodiments are not mutually exclusive. Rather, the artisan would recognize a myriad of combinations of some or all of such embodiments.

DETAILED DESCRIPTION

Overview

With an increasing number of patients receiving care at home, there is a growing need for high-quality home monitoring and telehealth equipment. Accordingly, systems, methods, and apparatuses for improved patient monitoring are described. A patient monitoring device can be configured to provide fast and reliable physiological measurements in a variety of care settings, including, but not limited to, at the patient's home. In some aspects, the patient monitoring device includes a compact, standalone monitor with telehealth capabilities, as well as an intuitive interface for use at home.

The patient monitoring device can provide real-time patient data to clinicians, which promotes timely, patient-centric care. For example, the patient monitoring device can be configured for patient surveillance. The device or system can include one or more integrated or external cameras, microphones, and/or audio devices to facilitate one- or two-way patient-physician/caregiver communication. The patient monitoring device can be configured to incorporate live video chat capabilities, which can facilitate discussions (for example, regarding, treatment, medications, therapy, or the like) between patients and caregivers or health practitioners.

The patient monitoring device can be configured to measure various physiological parameters. For example, the housing of the patient monitoring device can be sized to fit one or more of various modules (or internal components) that provide different physiological monitoring capabilities. In various configurations of patient monitoring device, the patient monitoring device can include any combination of the one or more modules. For example, each of the configurations can include a baseline set of physiological monitoring capabilities. The addition of a module to a patient monitoring device can increase the physiological monitoring capabilities of the patient monitoring device. Non-limiting examples of configurations include a Pulse CO-Oximeter configuration, a non-invasive blood pressure (NIBP) configuration (for example, including one or more capabilities of the Pulse CO-Oximeter configuration, plus NIBP capabilities), and a capnography configuration (for example, including one or more capabilities of the Pulse CO-Oximeter configuration, plus capnography capabilities). Each configuration can include the same or a similar housing or sleek design. However, each of the one or more configurations can include a different faceplate (for example, for attaching different sensors or probes) and/or different internal components (for example, including different modules). Accordingly, portions of the housing can be interchangeable between the multiple configurations, thereby streamlining the manufacturing process by reducing the number or parts or molds required to manufacture the housing parts.

The patient monitoring device can include a sleek and continuous outer surface that is easy to clean and relatively free of crevices, holes, or surfaces that collect external contaminants. For example, the housing of the patient monitoring device can include multiple portions that are configured to attach primarily using internal connection features, while using limited or no screws or screw holes. In addition, the housing of the patient monitoring device can connect with a display using similar internal connection features and using limited or no screws or screw holes. By limiting a number of screw holes, the housing has fewer crevices, thereby reducing the amount of dirt or other contaminants that are stuck in the housing.

Temperature regulation of an electrical device has an influence on the device's service life, surface temperature, functionality, and electric and fire safety, among other things. To combat this, a device can include one or more ventilation holes or openings that allow air to exhaust through the patient monitoring device. In some cases, a ventilation hole can allow external contaminants to enter the device, which can affect the device's functionality. Accordingly, systems, methods, and apparatuses for improved ventilation of a patient monitoring device are described.

The patient monitoring device can include a vent cover that can be configured to cover a ventilation hole without occluding (or only partially occluding) the ventilation hole and/or configured to provide a stabilization feature to the patient monitoring device. The vent cover can couple to a patient monitor such that a ventilation hole is at least partially covered but is not occluded (or is only partially occluded) by the vent cover. When coupled to the patient monitoring device, the vent cover is swivelable (for example, when rotated by a user) and can be swiveled between various configurations.

In a first configuration, the vent cover can protect the ventilation hole(s) from external contaminants, while still allowing air to vent from the ventilation hole. For example, the patient monitor may be positioned proximate the patient such that patient fluids or other substances are likely to come in contact with the patient monitor. The vent cover can shield the ventilation hole to keep these substances from entering the patient monitor through the ventilation hole. In the first configuration, the vent cover can be swiveled parallel to a lengthwise axis of the device. In addition or alternatively, the vent cover can fit within indentions of a recess defined by the housing of the patient monitoring device such that an outer surface of the vent cover is at least partially flush, level, or even with an outer surface of the housing. This maintains the sleek, smooth design of the patient monitoring device, making it easier to clean and more portable. The first configuration is useful when moving or storing the patient monitoring device, or when the patient monitoring device is operating in a landscape mode for example.

In a second configuration, the vent cover can act as a stand or other stabilizing feature for the patient monitoring device. For example, the vent cover can be swiveled perpendicular to the first configuration and perpendicular to a lengthwise axis of the device. While in the second configuration, the vent cover can provide support and stability to the patient monitoring device. For example, the vent cover can aid in stabilizing the patient monitoring device, particularly when the device is in a portrait mode and is less stable.

In any of the above-discussed configurations, the vent cover can be configured such that it does not prevent a flow of air through the ventilation hole. Accordingly, the vent cover advantageously provides a multipurpose advantage of the having both a shielding configuration (for example, the first configuration) and a supporting or stabilizing configuration (for example, the second configuration), each of which allows ventilation through the ventilation hole.

Alternatively, the patient monitor may not include and/or the vent cover may not cover a ventilation hole. Rather, in the first configuration, the vent cover (which, in this example is sometimes referred to as a swivel foot) can simply be configured to be oriented parallel to a lengthwise axis of the device and fit within indentions of a recess defined by the housing of the device. Further, an outer surface of the swivel foot can be at least partially flush, level, or even with an outer surface of the housing. This maintains the sleek, smooth design of the patient monitoring device, making it easier to clean and more portable. The first configuration can be useful when moving or storing the patient monitoring device, or when the patient monitoring device is operating in a landscape mode for example. However, as described above, the swivel foot may or may not be protecting a ventilation hole. The second configuration of the swivel foot can correspond to the second configuration as described herein. For example, the swivel foot can be swiveled between perpendicular to the first configuration and perpendicular to a lengthwise axis of the device. The second configuration can provide support and stability to the patient monitoring device. For example, the swivel foot can aid in stabilizing the patient monitoring device, particularly when the device is in a portrait mode and is less stable.

Patient Monitoring System

FIG. 1 illustrates a schematic block diagram of an example patient monitoring system 100. As illustrated, the system 100 can include a patient monitoring device 102 in wired or wireless communication (for example, via Bluetooth, Wi-Fi, or cellular) with a combination of one or more of a blood pressure module 104, a pulse oximetry module 106, a capnography module 108, a video or camera module 110, one or more remote modules 114, and/or a monitoring station 112. The one or more modules 104, 106, 108, 109, or 110 can be integrated or combined with the patient monitoring device 102. Additional, fewer, or different modules can be in communication and/or incorporated within the patient monitoring device 102. Furthermore, any of the modules or stations can communicate with any of the other modules or stations.

The patient monitor 102 (sometimes referred to as a point-of-care device) can serve as a connectivity hub for any of various device that can be collectively referred to as remote modules 114. For example, the patient monitor can be wired or wirelessly, for instance via Bluetooth, aggregate data from each of a plurality of remote modules 114. The patient monitor 102 can communicate with or integrate data from one or more devices such as a weight scale, glucometer, spirometer, stethoscope, a capnograph (such as the EMMA™ Capnograph marketed and sold by Masimo Corporation of Irvine Calif. ("Masimo")), a thermometer (such as the Caregiver marketed and sold by Masimo), a hemoglobin sensor (such as the Rainbow® DCI®-mini marketed and sold by Masimo), a pulse oximeter (such as the MightySat™ Rx marketed and sold by Masimo), etc.

The patient monitor 102 can advantageously include one or more ports for communicating with one or more sensors or sensor cables. For example, the patient monitor can include a port for communicating with a sensor configured to measure at least one parameter corresponding to oxygen saturation ($SpO_2$), pulse rate (PR), perfusion index (PI), total hemoglobin (SpHb®), methemoglobin (SpMet®), carboxyhemoglobin (SpCO®), oxygen content (SpOC®), oxygen reserve index (ORi®), pleth variability index (PVi®), acoustic respiration rate (RRa®), respiration rate from pleth (RRp™), fractional arterial oxygen ($SpfO_2$™), rainbow Pleth Variability Index (RPVi™), or signal quality. In addition or alternatively, the patient monitor 102 can include a port for communicating with a blood pressure sensor, such as a non-invasive blood pressure (NIBP) measuring device such as an arm cuff. In addition or alternatively, the patient monitor 102 can include a port for communicating with a capnography sensor (for example, a $CO_2$ sensor) so as to measure or determine parameters such as end-tidal carbon dioxide (etCO2), SpO2, NIBP, Predictive or Temporal Artery Temperature, Masimo Rainbow® parameters (for example, RRa™, SpCO®, PVi®), 3-Lead electrocardiogram (ECG) etc. The patient monitor 102 can include a port for communicating with a biopotential sensor, a respiratory rate sensor, or a glucose sensor. The patient monitor 102 can wirelessly communicate with sensor modules such as a blood pressure module, a pulse oximetry module, or a capnography module.

As a non-limiting example, the patient monitor 102 includes a sensor interface, a signal processor, and a transceiver. The patient monitor 102 receives a sensor signal associated with a sensor, for example, corresponding to a blood pressure module 104, pulse oximetry module 106, capnography module 108, remote module 114, or other module configured to measure one or more parameters which can be utilized for calculation or determination of physiological parameters. Depending on the sensor, the patient monitor 102 provides one or more drive signals to the sensor. The patient monitor 102 can receive (through wired or wireless connection) the sensor signal and can determine a conditioned signal The conditioned signal may be transmitted or further processed by a signal processor, such as buffering, digital filtering, smoothing, averaging, adaptive filtering and frequency transforms to name a few. The signal processor can derive a parameter or value responsive to the sensor signal. The resulting parameter signal may be a measurement calculated or derived from the conditioned signal, such as $SpO_2$, PR, Pi, blood pressure, or any of the physiological parameters described herein. In some instances, the parameter signal may be an intermediate result from which the above-stated measurements may be calculated or derived.

The patient monitor 102 may be battery powered or externally powered from an independent AC or DC power source. For example, the patient monitor 102 can include an internal rechargeable battery such as a lithium ion (Li-on) battery. The patient monitor can be configured to function for up to or more than 7 hours on a single battery charge. The battery can recharge from a state of no charge to a state of full charge in approximately 3 hours.

Patient Monitoring Device Configurations

Figure 2A:
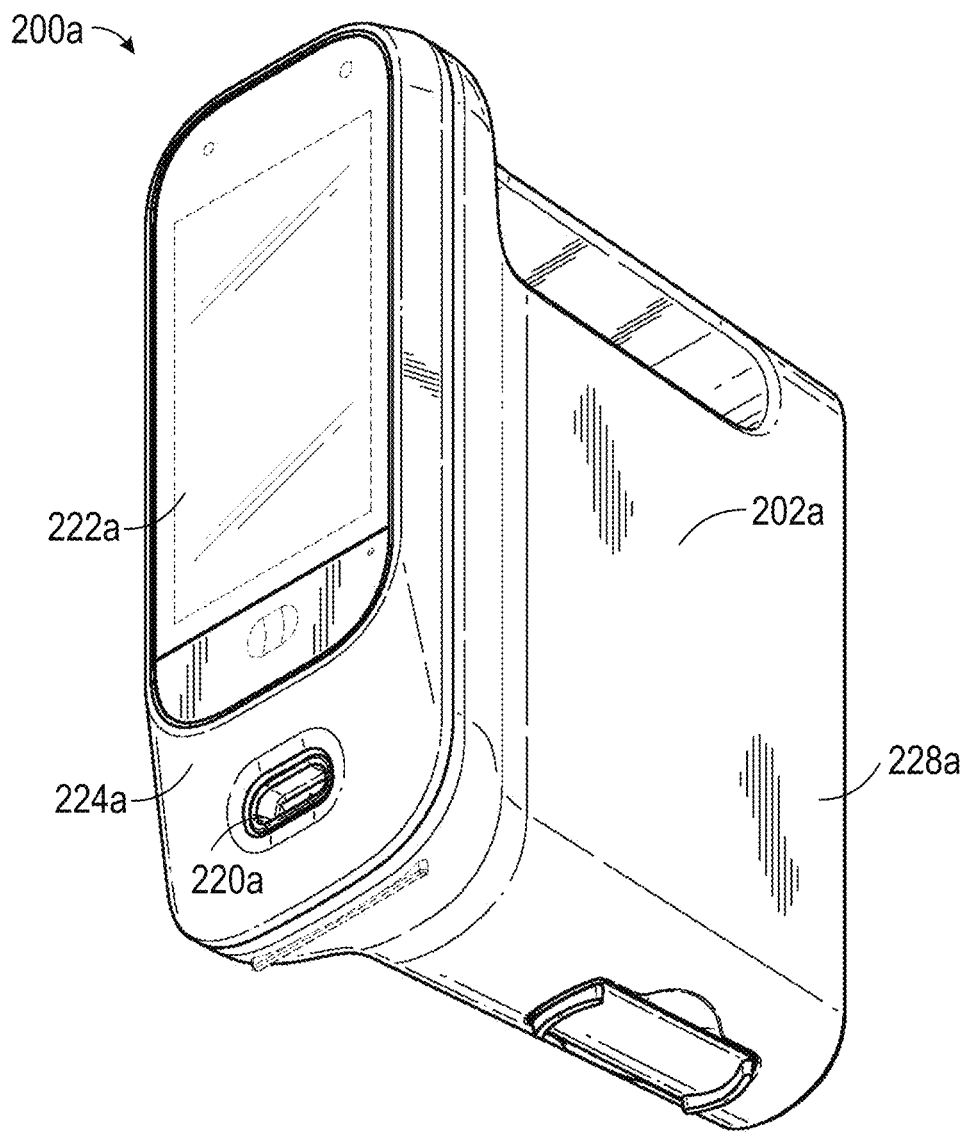
FIGS. 2A-2C illustrate various example configurations of a patient monitoring device.
Figure 2B:
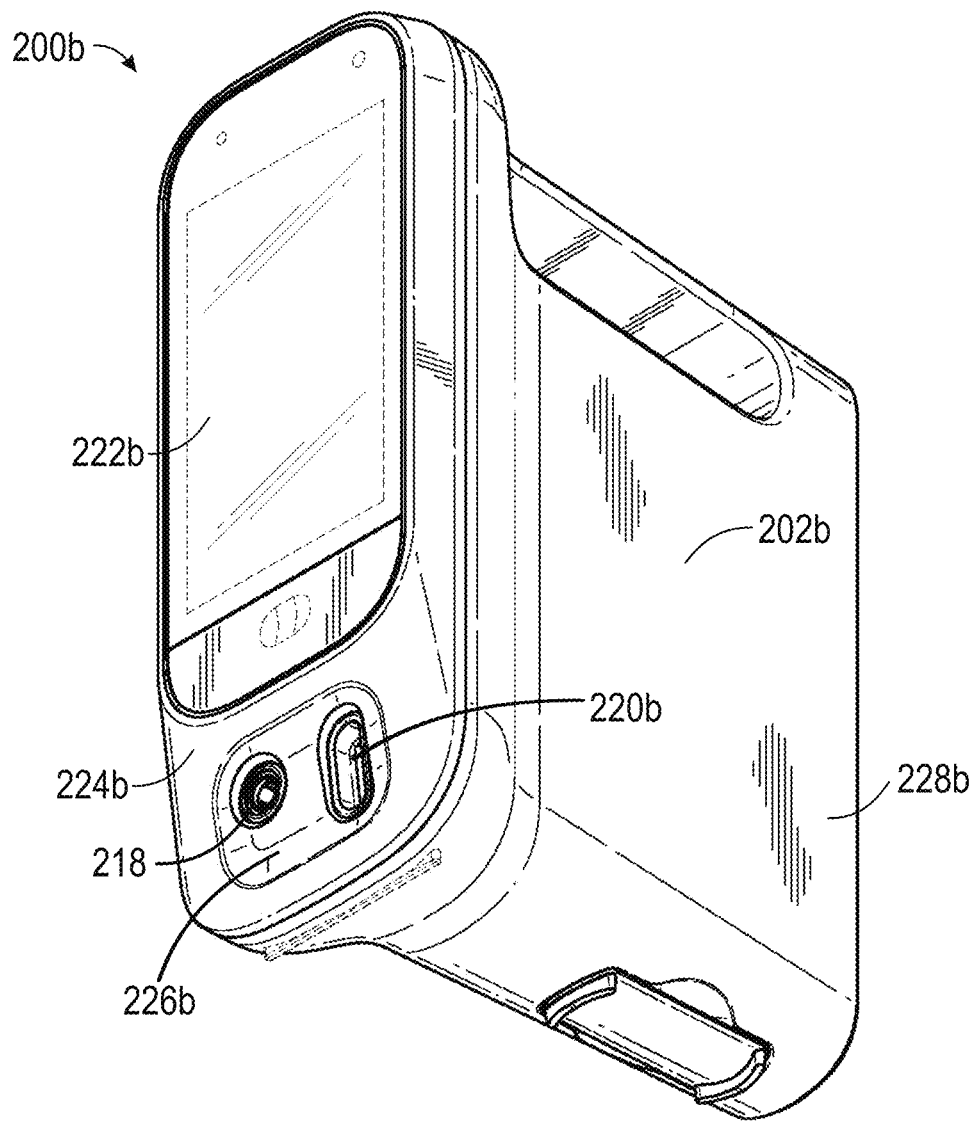
Figure 2C:
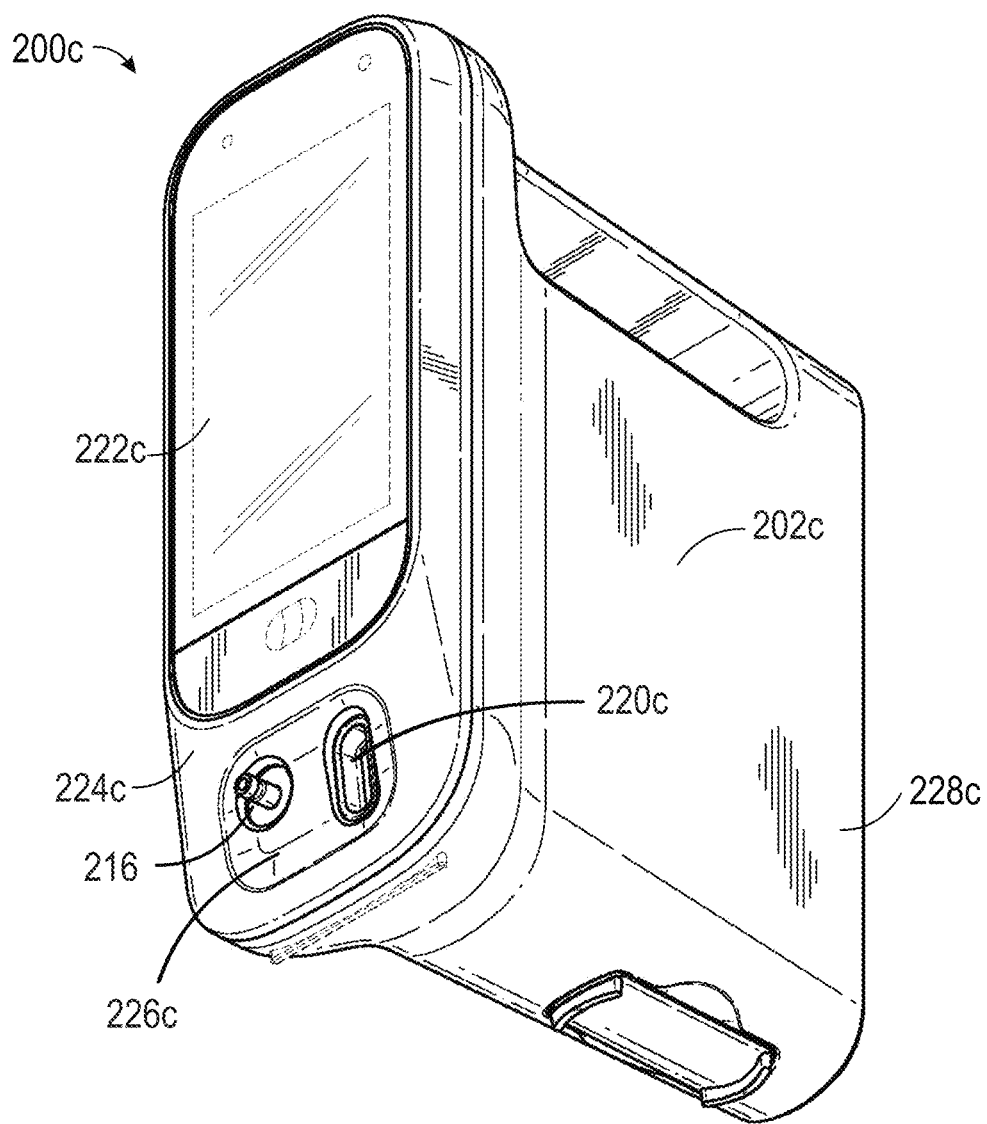

FIGS. 2A-2C illustrate various example configurations of a patient monitoring device. As described herein, as compared to a baseline configuration (for example, the Pulse CO-Oximeter Configuration of FIG. 2A), some configurations of the patient monitoring device can allow for monitoring of one or more additional, fewer, or different physiological parameters.

Advantageously, one or more of the configurations illustrated in FIGS. 2A-C include a similar housing or chassis. Accordingly, portions of the housing can be interchangeable between the configurations. The back portions of the housings of each of the configurations can be identical or substantially similar. For example, the back portion 228c of the configuration of FIG. 2C can be interchangeable with the back portion 228a or 228b of the configurations of FIG. 2A or 2B. However, in some cases, the back portions may differ. In addition or alternatively, front portions of the housing can be interchangeable between the configurations. For example, the front plate 224c of the configuration of FIG. 2C can be interchangeable with the front plate 224a/224b of the configurations of FIG. 2A or 2B. However, in some cases, the front plates may differ. Having interchangeable portions of the housing or chassis can advantageously streamline the manufacturing process by reducing the number or parts or molds required to manufacture the housing parts. Furthermore, although the housings are similar or identical, the internal components of the multiple configurations can include similar, different, fewer, or additional components.

Pulse CO-Oximeter Configuration

FIG. 2A illustrates an example configuration of a patient monitoring device 200a. As shown, the patient monitoring device 200a can be a standalone monitor 200a. The standalone monitor 200a includes a housing 202a, integrated display 222a, faceplate 224a, and sensor port 220a. In some cases, this configuration is referred to as a Pulse CO-Oximeter configuration.

The sensor port 220a can be configured to electrically connect with a sensing device, such as a pulse oximetry sensor, or corresponding cable. Based on a signal received from a sensing device, the patient monitoring device 202a can determine one or more physiological parameters. For example, the physiological parameters can include, but are not limited to, oxygen saturation (SpO2), pulse rate (PR), perfusion index (Pi), and/or pleth variability index (PVi®). In addition or alternatively, the physiological parameters can include total hemoglobin (SpHb®), methemoglobin (SpMet®), carboxyhemoglobin (SpCO®), oxygen content (SpOC®), oxygen reserve index (ORi®), acoustic respiration rate (RRa®), respiration rate from pleth (RRp™), rainbow Pleth Variability Index (RPVi™), fractional arterial oxygen (SpfO2™), and/or or signal quality. In some cases, the patient monitoring device 202a can be configured to determine some, if not all, of the physiological parameters listed above. For example, the patient monitoring device 202a can be upgraded or downgraded to have the capability to monitor only particular parameters. In some cases, one or more calculations can be performed on the sensing device, and the patient monitoring device 202a can receive one or more signals indicative of physiological parameters.

Noninvasive Blood Pressure (NIBP) Configuration

FIG. 2B illustrates an example NIBP configuration of a patient monitoring device 200b. Similar to the patient monitoring device 202a of FIG. 2A, the patient monitoring device 202b includes a housing 202b, an integrated display 222b, a faceplate 224b, and a sensor port 220b. Furthermore, the patient monitoring device 200b includes a port 218 for connecting a blood pressure sensing device. As shown, the faceplate 224b can be different from faceplate 224a of FIG. 2A, for example, to accommodate ports 220b and 218. In some cases, this configuration is referred to as an NIBP Configuration.

The patient monitoring device 200b can provide some or all of the capabilities of a Pulse CO-Oximeter, such as those described herein with respect to FIG. 2A. For example, the physiological parameters can include, but are not limited to, oxygen saturation (SpO2), pulse rate (PR), perfusion index (Pi), and/or pleth variability index (PVi®), total hemoglobin (SpHb®), methemoglobin (SpMet®), carboxyhemoglobin (SpCO®), oxygen content (SpOC®), oxygen reserve index (ORi®), acoustic respiration rate (RRa®), respiration rate from pleth (RRp™), rainbow Pleth Variability Index (RPVi™), fractional arterial oxygen (SpfO2™), and/or or signal quality. For example, the port 220b can correspond to port 220a of FIG. 2A, and the patient monitoring device 220b can be configured to determine any of these various physiological parameters based on a signal received from a sensor attached to port 220b.

In addition, the patient monitoring device 200b can provide blood pressure monitoring capabilities. The patient monitoring device 200b can be integrated with port 218 for connecting a blood pressure sensing device. For example, integrated port 218 can be configured to connect to blood pressure cuff (for example, via an inflation hose). The port 218 can be compatible with any of disposable or reusable blood pressure cuffs, for adult, pediatric, and/or neonatal patients.

The patient monitoring device 200b can be configured to measure blood pressure between the range of 0 mmHg and 300 mmHg. The blood pressure measurements can provide blood pressure reading accurate within 1, 2, 3, 4, 5, or 10 mmHg. The patient monitoring device 200b can be configured to provide "spot-check" blood pressure measurements, which can allow for a single, user-imitated measurement. The spot-check measurements can be taken at various times throughout the day. The patient monitoring device 200b can be configured to routinely take blood pressure measurements (for example, at a desired interval), eliminating a need to do so manually. Furthermore, the patient monitoring device 200b can be configured to continuously measure blood pressure for a desired duration, such as 5 or 10 minutes. As described in more detail herein, a value or display associated with any parameters or corresponding waveforms can be displayed on display 222b.

Capnography Configuration

FIG. 2C illustrates an example Capnography configuration of a patient monitoring device 200c. Similar to the patient monitoring device 202a of FIG. 2A, the patient monitoring device 202c includes a housing 202c, an integrated display 222c, a faceplate 224c, and a sensor port 220c. Furthermore, the patient monitoring device 200c includes a connector 216 for connecting one or more Capnography-related sensors (for example, via a hose). As shown, the faceplate 224b can be different from faceplate 224a of FIG. 2A, for example, to accommodate ports 220a and 218. In some cases, the faceplate 224c can be different or the same faceplate as faceplate 224b of FIG. 2B. This configuration can be referred to as a Capnography configuration or an ISA configuration.

The patient monitoring device 200c can provide some or all of the capabilities of a Pulse CO-Oximeter, such as those described herein with respect to FIG. 2A. For example, the physiological parameters can include, but are not limited to, oxygen saturation (SpO2), pulse rate (PR), perfusion index (Pi), and/or pleth variability index (PVi®), total hemoglobin (SpHb®), methemoglobin (SpMet®), carboxyhemoglobin (SpCO®), oxygen content (SpOC®), oxygen reserve index (ORi®), acoustic respiration rate (RRa®), respiration rate from pleth (RRp™), rainbow Pleth Variability Index (RPVi™), fractional arterial oxygen (SpfO2™), and/or or signal quality. For example, the port 220c can correspond to port 220a of FIG. 2A, and the patient monitoring device 220c can be configured to determine any of these various physiological parameters based on a signal received from a sensor attached to port 220c.

The patient monitoring device 200c can include an integrated ISA CO2 module and a capnography connector 216, which can enable the patient monitor 220c to monitor aspects of CO2. For example, patient monitor can monitor end-tidal carbon dioxide (EtCO2) monitoring and can display numeric, trend, and/or waveform data on the display 222c. In addition or alternatively, patient monitoring device 200c can monitor fractional concentration of inspired carbon dioxide (FiCO2) and/or respiration rate (RR). The patient monitor 220c can display on display 222C a capnogram waveform or a $CO_2$ trend waveform, among other data.

Integrated Display

Figure 3A:
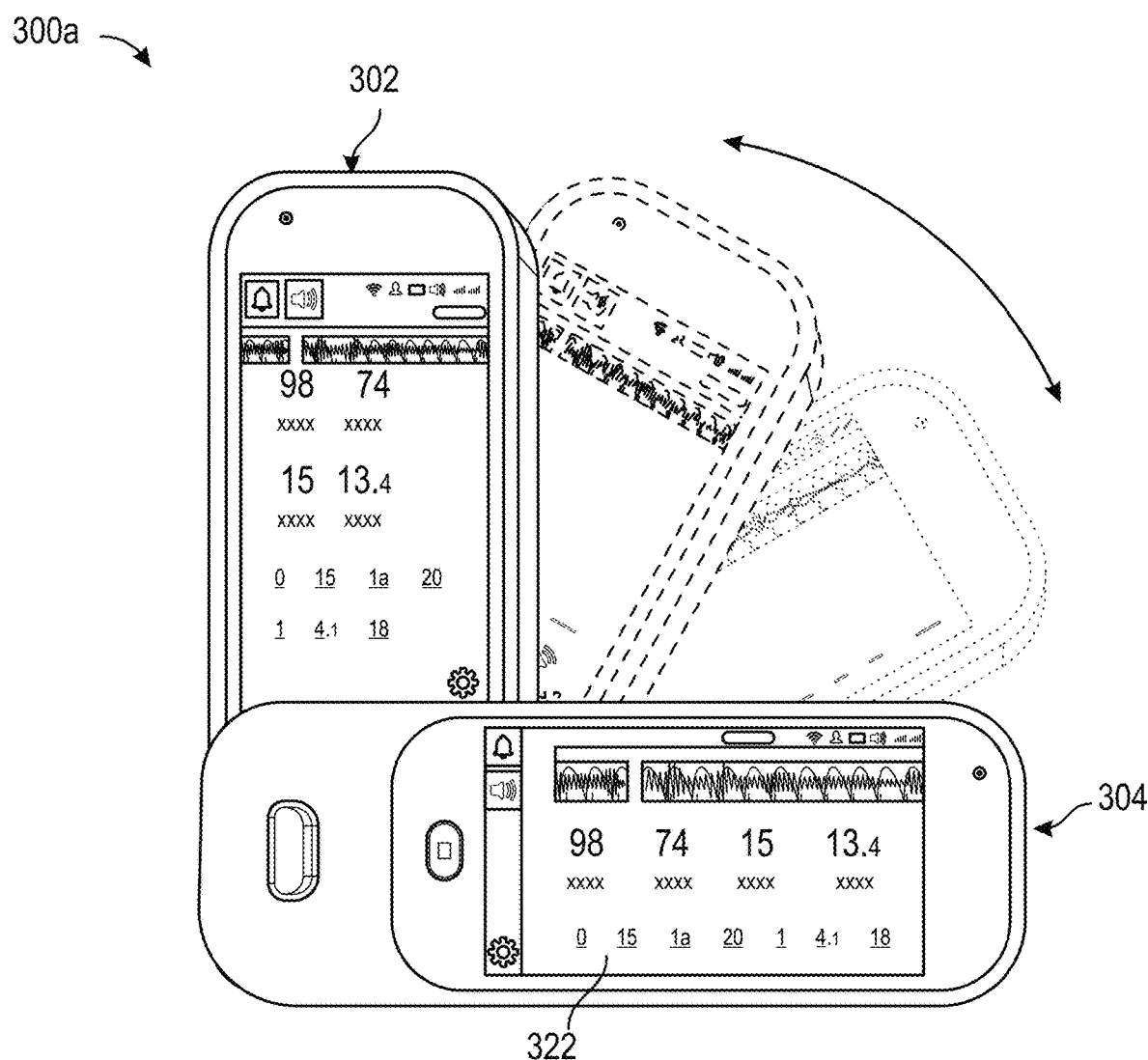
FIGS. 3A-3B illustrate example patient monitoring devices.

FIG. 3A illustrates an example patient monitoring device 300a. As shown, the patient monitoring device 300a can include an integrated display 322. The display 322 can be customizable such that a user can choose which information to display on the display 322. For example, the user can choose to display one or more of various waveforms, trends, values, timelines, or other data related to a patient's physiological status. The display 322 can include touch screen capabilities. For example, a user can adjust a range of a displayed trend time by using intuitive fingers gestures (for example, pinching or spreading his or her fingers).

In some cases, the display 322 can display in portrait mode 302 or landscape mode 304, and can transition between display modes, for example, based on the orientation of the monitor 300a. For example, the patient monitor can determine its orientation using a gyroscope or an accelerometer. Based on its determined orientation, the patient monitoring device 300a can display in landscape or portrait mode. The display may display partially in portrait mode and partially in landscape mode. The display 322 can display in portrait mode when oriented vertically and can display in landscape mode when oriented on its side. A user can select landscape or portrait mode, which can cause the display to lock the display in the selected mode despite the orientation of the patient monitoring device 300a.

Figure 3B:
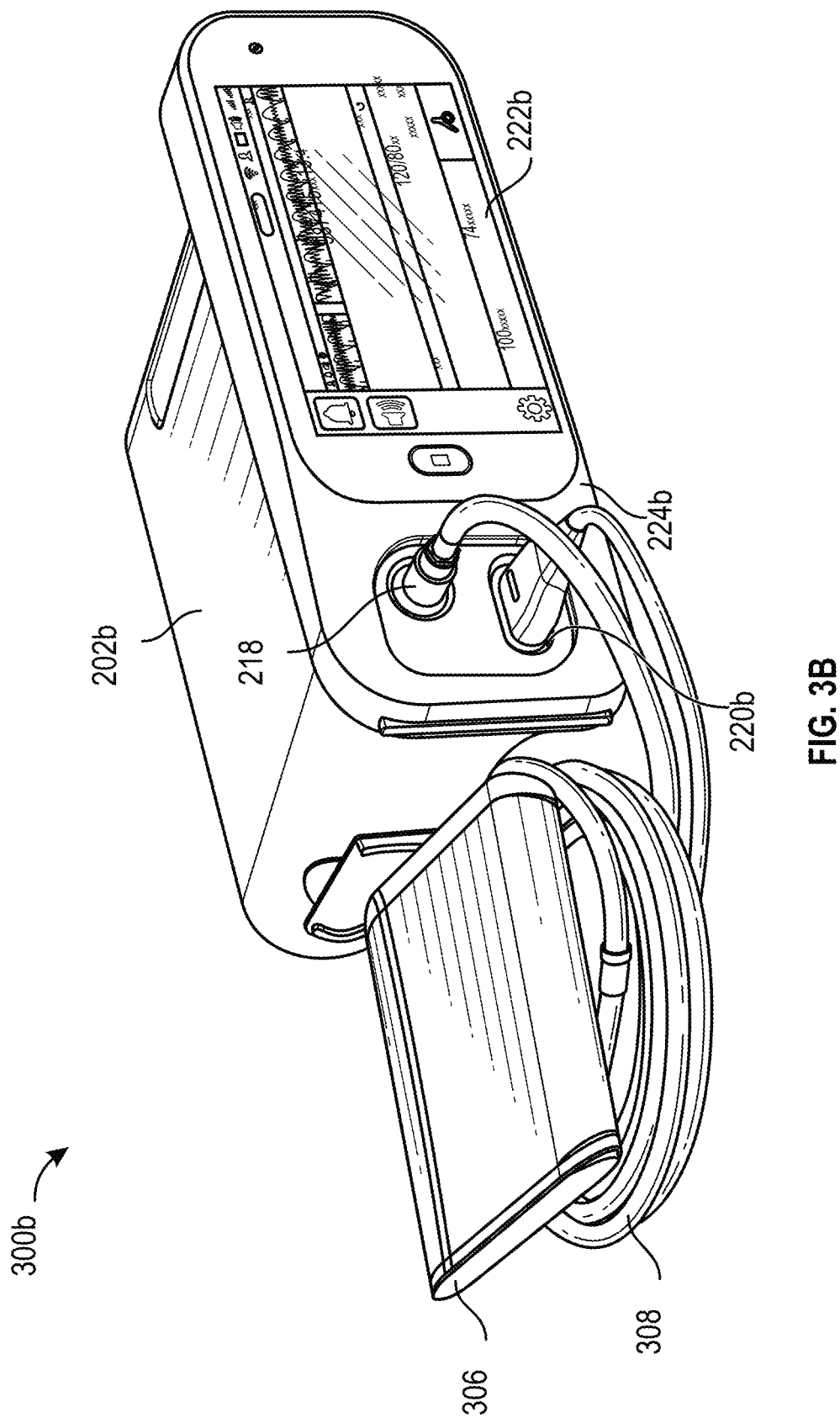

FIG. 3B illustrates an example patient monitoring device 300b. As described herein with respect to FIG. 2B, the patient monitoring device 300b can be configured in an NIBP configuration. For example, the patient monitoring device 300b can include a housing 202b, an integrated display 222b, a faceplate 224b, a sensor port 220b, and a port 218 for connecting a blood pressure sensing device 306 (for example, via hose 308). The blood pressure sensing device 306 can include a combination of one or more of a disposable or reusable blood pressure cuff that can be configured for adult, pediatric, and/or neonatal patient use.

Two-Way Consultation

Figure 4A:
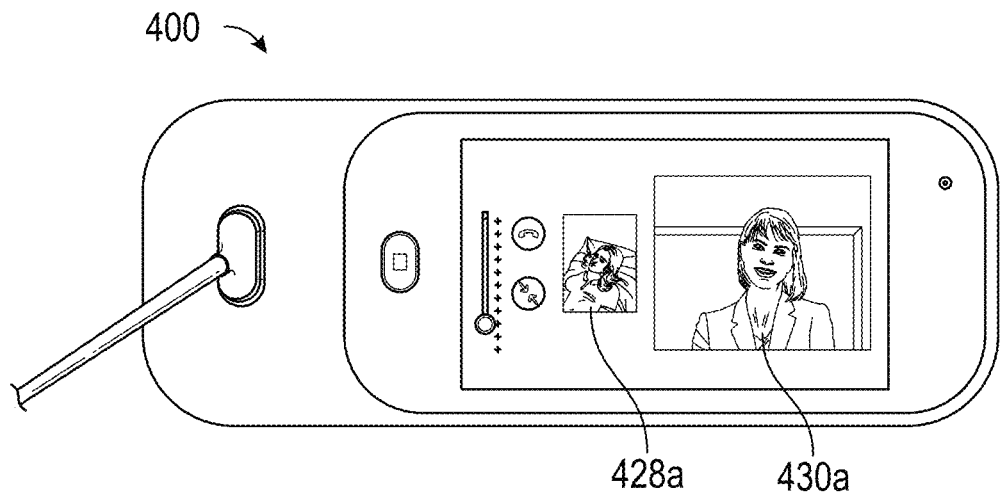
FIGS. 4A-4B illustrate an example patient monitoring system configured for two-way consultation.
Figure 4B:
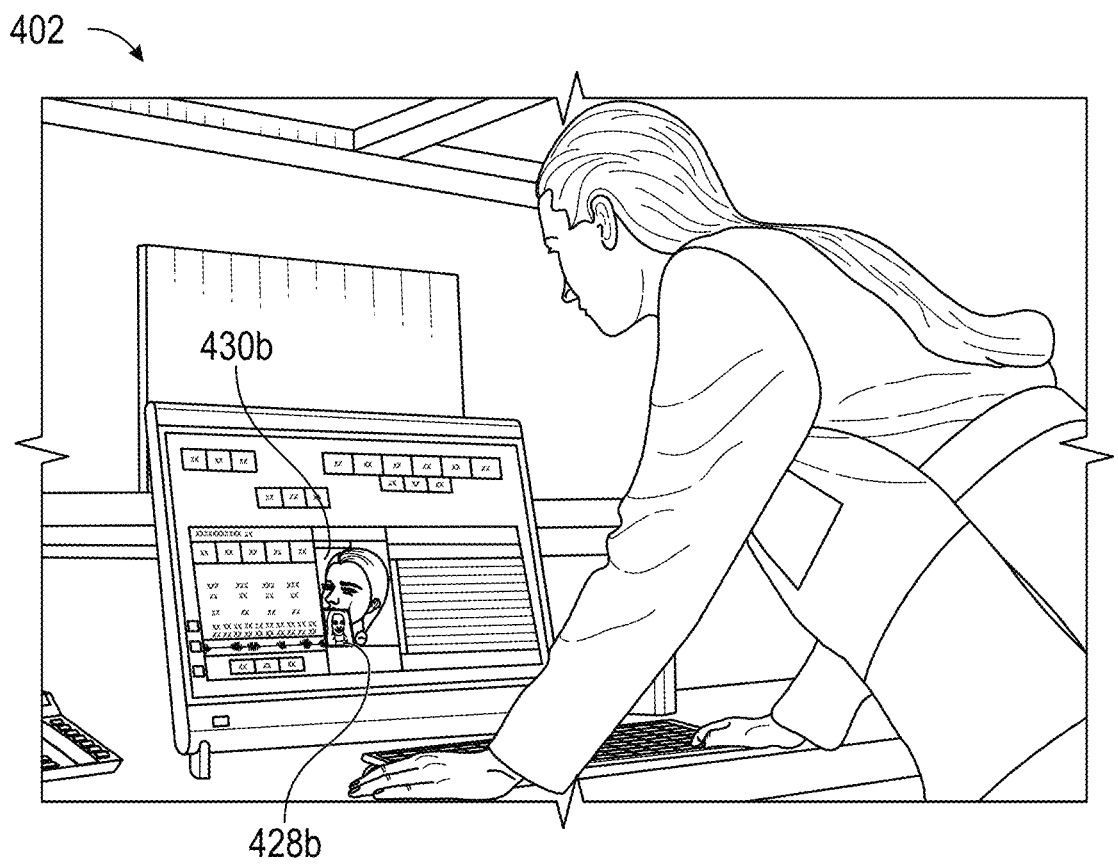

FIGS. 4A-4B illustrate an example patient monitoring system configured for two-way consultation. The patient monitoring system can provide real-time virtual one- or two-way consultation using integrated video capabilities. For example, the patient monitoring system can include a high-definition camera, which can enable live, high-resolution video and audio feeds directly from a point-of-care device 400 to a central viewing station 402 or smart device, thereby allowing caregivers to provide on-demand care and/or support. The cameras can facilitate one- and two-way patient-caregiver communication. The one- or two-way consultation (sometimes referred to as videoconferencing) advantageously provides a medium for on-demand care and aids in proactively determining when an in-person visit is desired or necessary. For example, one-way, surveillance monitoring can enable a caregiver to observe patient movements and listen to breathing for virtual assessment without disturbing the patient.

The patient monitoring system can cause a display to display in real-time a video or image of a patient 428a, 428b and/or a real-time video or image of a caregiver 430a, 430b. The videos or images can include high-definition video (for example, 1080i, 1080p, 4 k, etc.), and in some cases, the cameras can be integrated directly into the patient monitoring device 400, eliminating the need to purchase additional modules or infrastructure. In some cases, the system utilizes a video surveillance system, such as Masimo's SafetyNet Surveillance.

The patient monitoring device 400 can be configured to facilitate the transmission of patient data and/or the transmission of live video conferencing. For example, the patient monitor can share video and/or patient data to one or more of clinicians, caregivers, electronic medical records, or a monitoring station 402. Accordingly, the patient monitoring device 400 can advantageously serve as an integrated solution for patient data gathering and/or transmission. In some cases, the system can utilize an existing hospital IT network and can provide viewing of images in the same care area. Accordingly, the system can provide for real-time video and/or audio communication that can improve the quality and safety of patient care.

The real-time video images of a patient's room and/or a monitoring station can be gathered using, for example, an integrated or remote camera. For example, a camera associated with patient monitor 400 can deliver a high-resolution, high-frame rate video feed to the patient monitoring device 400 or a viewing station 402. Similarly, a camera associated with viewing station 402 can deliver a high-resolution, high-frame rate video feed to the patient monitoring device 400 or a viewing station 400. In some instances, the system can include an external mechanical lens cap lets the patient or his visitors disable or cover the camera at any time.

In addition or alternatively, the video feed or images presented at the patient monitoring device 400 or a viewing station 400 can include one or more physiological parameters. For example, the one or more physiological parameters can be overlaid on and/or positioned around (for example, in a separate window) the live video feed such that the patient and/or caregiver can view both the video feed and the physiological parameters. In some cases, the physiological parameters can be presented on a separate display that is different from the display presenting the real-time video images.

Vent Cover

Figure 5:
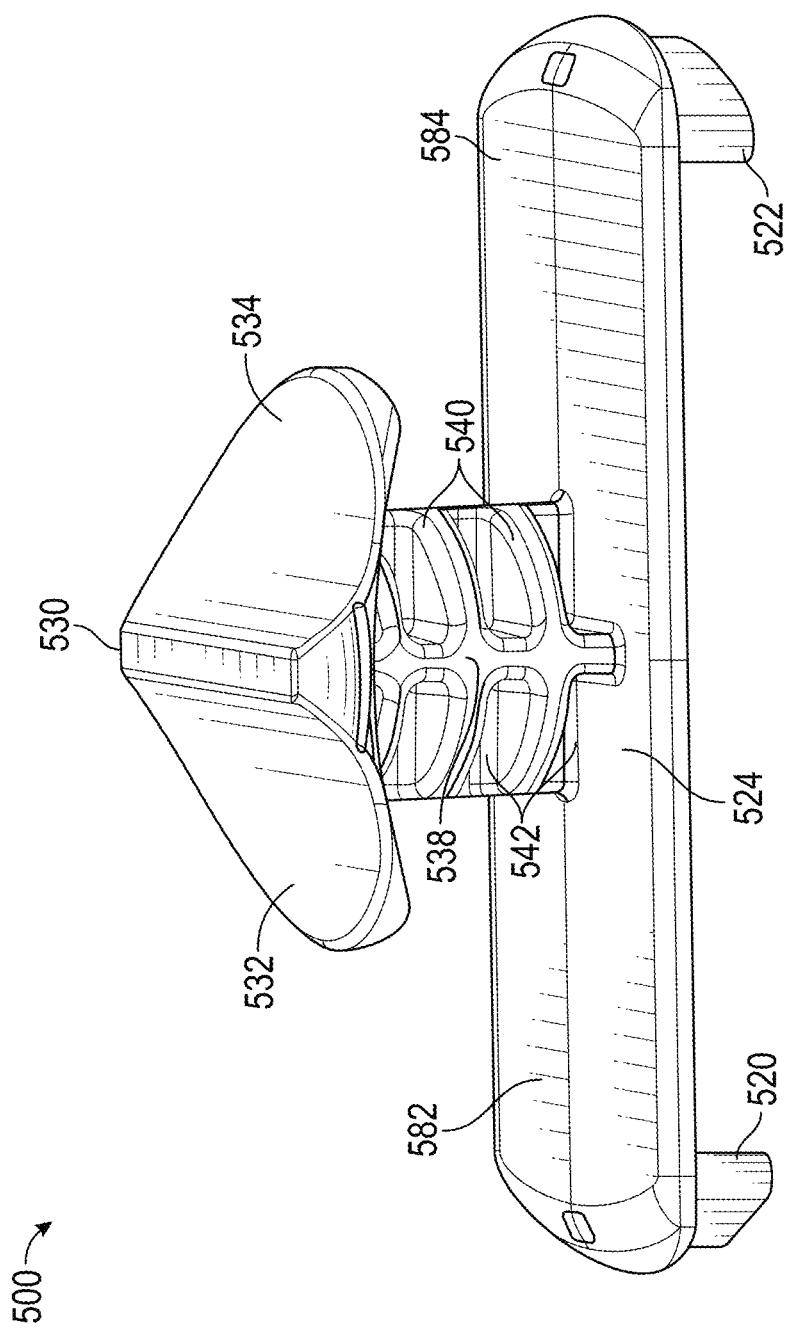
FIG. 5 illustrates an example vent cover for a patient monitoring device.

FIG. 5 illustrates an example vent cover for a patient monitoring device. The vent cover 500 can include a body 524, an extension member 538, and an engagement member 530. The extension member 538 can extend between the body 524 and the engagement member 530.

The body 524 can be relatively flat and can have a length which is longer than its width. For example, the length of the body 524 can be about 1.25, 1.5, 1.75, 2, 2.25, 2.5, 2.75, 3, 3.5, 4, 4.5, or 5 times the width of the body 524. Alternatively, the length of the body 524 can be approximately equal to the width of the body 524. The length and/or width of the body 524 can depend on the size of the patient monitoring device to which it will be attached. The body 524 can have a rectangular, curved rectangular or other shape. The body 524 can have a relatively constant length and/or width. Alternatively, the width and/or length may not be constant across the body 524. For example, a middle of the body 524 may be thin or thick relative to the outer edges of the body 524.

The extension member 538 extends away from the body the extension member 538 can extend from the body 524 at an angle of roughly 90° degrees (for example, 90° from a longitudinal plane of the vent cover 500). However, other angles are possible, such as 30°, 40°, 50°, 60°, 70°, 80°, 100°, 110°, 120°, 130°, 140°, 150°, 160° (+/−a few degrees).

The extension member 538 can be generally cylindrical or have substantially rounded sides, for example, to facilitate rotation of the vent cover 500 about an axis of the extension member 538. However, it should be understood the extension member can have any suitable shape. The extension member 538 can include one or more substantially flat sides which can advantageously limit undesired rotation of the vent cover 500. For example, a portion of the vent cover can be disposed within a hole (for example, hole 616 of FIG. 6) of a patient monitor such that the extension member 538 is framed by the exterior of the hole. The extension member 538 may have a flat side which corresponds to a flat portion of the hole. When the flat portions are aligned, the vent cover 500 can be in a desired configuration. Thus, the flat side may advantageously provide a locking feature which can limit movement (for example, rotation) of the vent cover 500.

Although illustrated as an extension from the center of the vent cover 500, the extension member 538 can extend from or be attached to any location on the vent cover 500. For example, the extension member 538 can extend from end 582 or end 584 or a corner of the body 524. Alternatively, the vent cover 500 can include two extension members 238, which can extend from each end 582, 584 of the body.

The extension member 538 can be substantially rigid or flexible. For example, the extension member 538 may be configured to bend relative to the body 524 or the engagement member 530. The extension member 538 includes a plurality of ribs 540 or rib-like features. The ribs can provide additional support or flexibility to the extension member 528 of the vent cover 500. In addition, the ribs 540 can define a plurality of cavities 542 between the ribs 540. In addition to providing room for the ribs 540 to flex, in some cases, the cavities 542 can provide a pathway for air to escape or enter the patient monitoring device while the vent cover 500 is attached to a patient monitoring device. The cavities 542 can permit air to flow through or around the vent cover 500, thereby facilitating exhaust of the patient monitoring device.

The vent cover 500 can include one or more feet 520, 522 disposed on the bottom of the body 524. The feet can be rubber or composed of any suitable material. The feet can provide a non-slip and/or non-scratch surface to the vent cover 500. The feet 520, 522 can be retractable, foldable, or otherwise adjustable to provide a more compact or sleek appearance, for example, when position in the first configuration. The feet 520, 522 can extend the width of the vent cover. Alternatively, the feet 520, 522 can be thinner or wider than the vent cover. Although illustrated as having two feet 520, 522, the vent cover can include fewer or more feet. In some cases, the vent cover does not include any feet.

The vent cover 500 can be generally composed of metal alloys, plastic, or other suitable material and can be made by conventional machining and metal fabrication techniques, plastic fabrication techniques, and finishing processes including but not limited to milling, lathing, electro discharge and welding, injection molding, powder coating and painting. The vent cover 500 can be coated with one or more coatings, including but not limited to plastic, rubber, powder coat and paint or any combination thereof. The combination of the vent cover 500 and a housing of a patient monitoring device (as described herein) can include multiple parts assembled or disassembled and delivered to its intended user. For example, an intended user can insert engagement member 530 of the vent cover 500 into or remove it from an aperture defined by the housing.

Patient Monitoring Device without Vent Cover

Figure 6A:
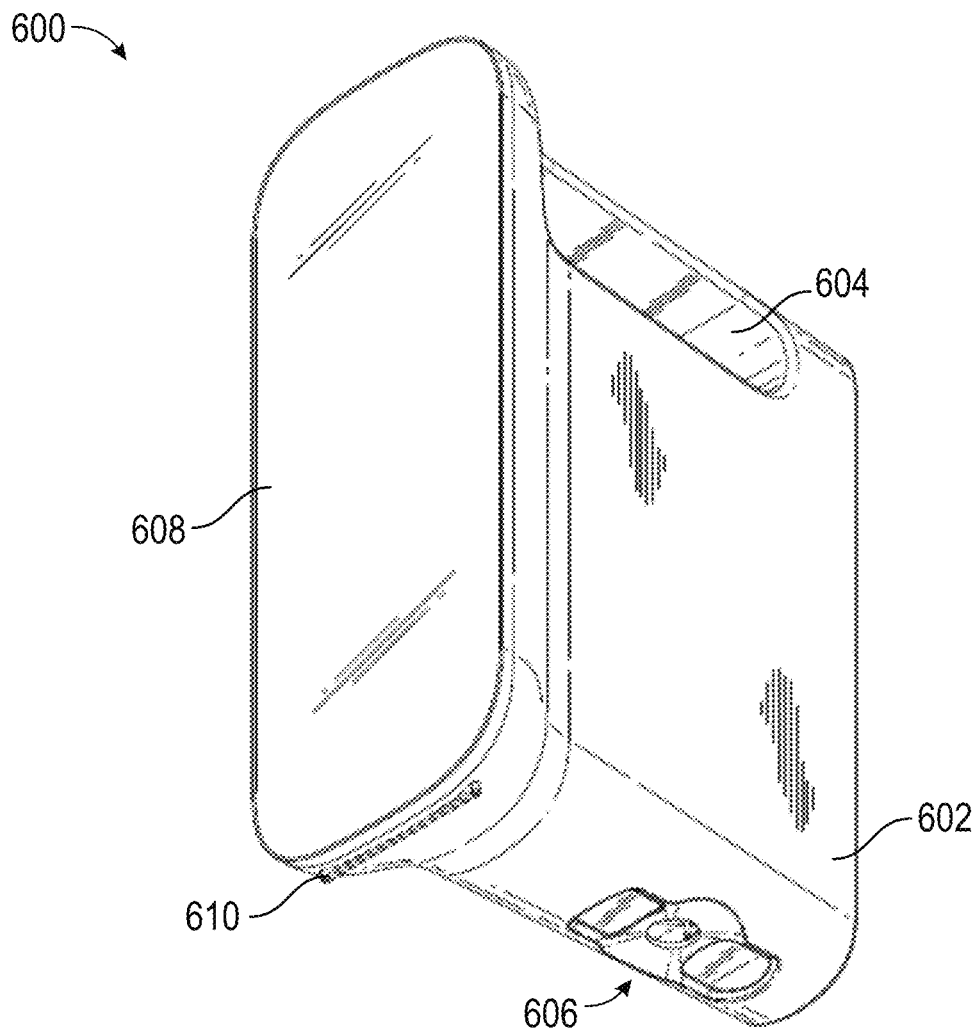
FIG. 6A illustrates an example a patient monitoring device configured to couple to the vent cover of FIG. 5.

FIG. 6A illustrates an example a patient monitoring device configured to couple to the vent cover of FIG. 5. As illustrated, the patient monitoring device 600 can include a display 608, a housing 602, a carrying handle 604, a protrusion 610 (sometimes referred to as a foot), and a section 606 for coupling and/or interfacing with a vent cover, such as vent cover 500 of FIG. 5.

The patient monitoring device 600 can be configured to sit upright (sometimes referred to as portrait mode) such that it rests on a bottom side. The housing 602 can include one or more protrusions 610 upon which the patient monitoring device 600 can be set. Further, the patient monitoring device 600 can include section 606 for interfacing with a vent cover, which may also aid in keeping the patient monitoring device upright.

The patient monitoring device 600 can include a carrying handle 604. For example, the housing 602 can define an aperture and the carrying handle 604 can be defined as the portion of the housing 602 between the aperture and the top of the patient monitoring device 600. In some instances, the aperture is approximately sized to fit a palm of a user's hand such that the user can grasp the handle by inserting his fingers into the aperture. The aperture can be larger, smaller, or about the size of the palm of a user's hand. For instance, the aperture can be sized to fit a user's arm such that the patient monitoring device 600 can be carried by, for instance, inserting a user's forearm into the aperture. The handle 604 can be advantageously positioned near the top of the patient monitoring device 600 to allow for easy carrying. However, it should be noted that the handle 604 can be positioned in any suitable location on the patient monitoring device 600.

Figure 6B:
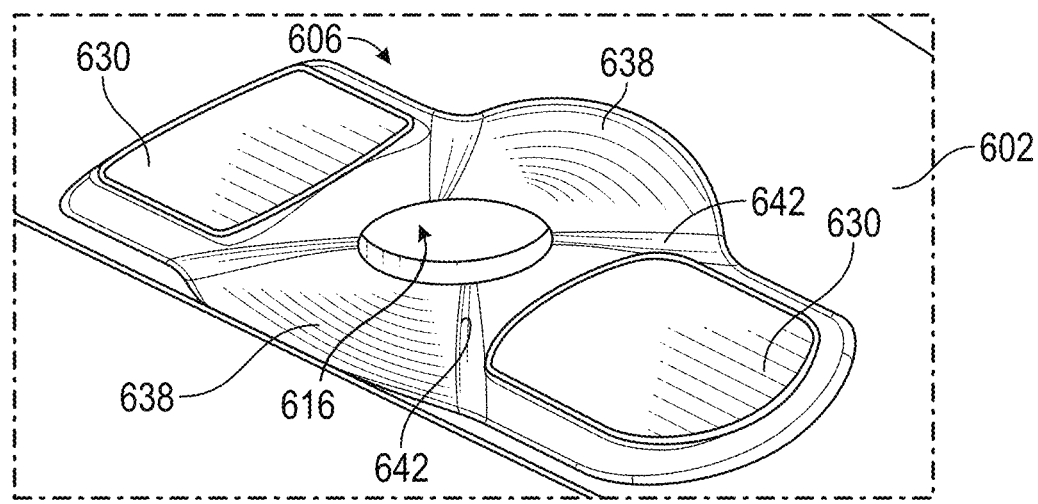
FIG. 6B illustrates a detail view of the section of FIG. 6A for coupling and/or interfacing with a vent cover.
Figure 8A:
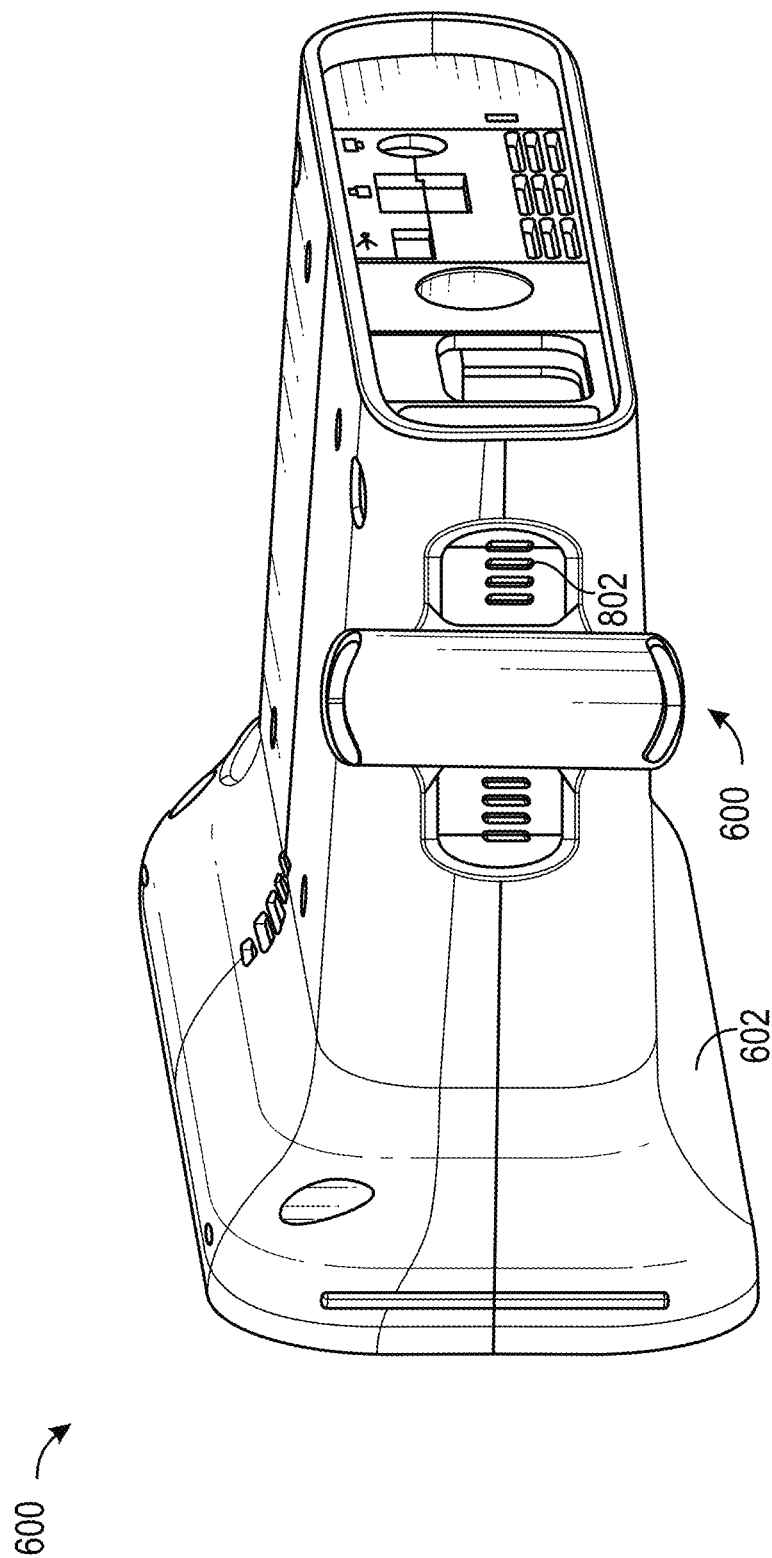
FIGS. 8A-8C illustrate an example patient monitoring device configured in a second configuration, according to some embodiments.

FIG. 6B illustrates a detail view of the section 606 for coupling and/or interfacing with a vent cover. As shown, the section 606 includes a plurality of indentations 630, 638 and a defined hole 616. In addition to acting as a connection point for a vent cover, the hole 616 can act as a ventilation hole to allow airflow though the patient monitoring device. In some cases (as illustrated in FIG. 8A), the recess 606 can include one or more ventilation holes 802 for additional airflow.

Referring to FIGS. 5 and 6B, the vent cover 500 can be coupled to the patient monitoring device 600 through hole 616 such that the hole encompasses the extension member 538. For example, the engagement member 530 can be inserted into hole 616. The engagement member 530 can include one or more flexible wings 532, 534 that cause the engagement member 530 to extend wider than the hole 616. For example, the engagement member 530 can be fit into the hole 616 by flexing or bending the wings 532, 534 (for example, towards the body 524) such that the width of the engagement member 530 is reduced and the engagement member 530 can fit into the hole 616. Upon insertion of the engagement member 530 into the hole 616, the flexible wings are configured to un-flex and act as an anchor to prevent the vent cover 500 from uncoupling from the housing 606. However, it will be understood that the vent cover 500 can be coupled to the patient monitoring device in various ways, such as during assembly of the patient monitoring device.

As illustrated, the housing 602 can define a plurality of raised indentions 642 between indentations 630, 638. The raised indentions 642 can function to stabilize the patient monitoring device by providing support to the vent cover 500 during the second configuration. In addition or alternatively, the raised indentions 642 can function as a locking feature which provides a barrier between configurations.

The indentations 630 and/or 638 can function as an exhaust feature. For example, while in a first configuration, indentations 638 may have a greater depression (for example, deeper) than the body of the vent cover 500. Thus, a space can exist under the vent cover 500, which can permit ventilation. For example, the space can provide an air passageway into the interior of the patient monitoring device. Similarly, while in a second configuration, indentations 630 may have a greater depression (for example, deeper) than the body of the vent cover 500. Thus, a space can exist under the vent cover 500, which can permit ventilation.

First Configuration

Figure 7A:
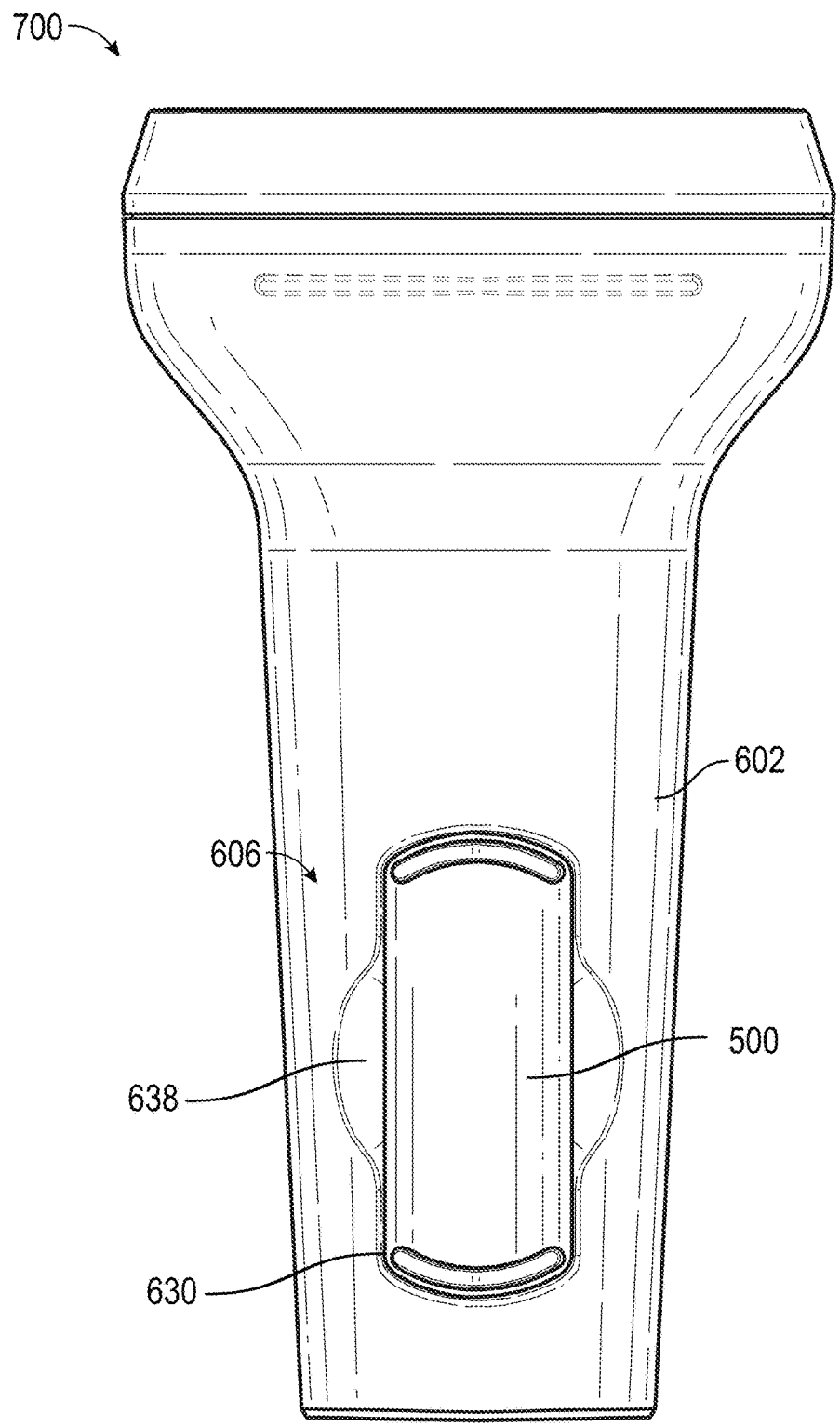
FIGS. 7A-7C illustrate an example patient monitoring device configured in a first configuration, according to some embodiments.
Figure 7B:
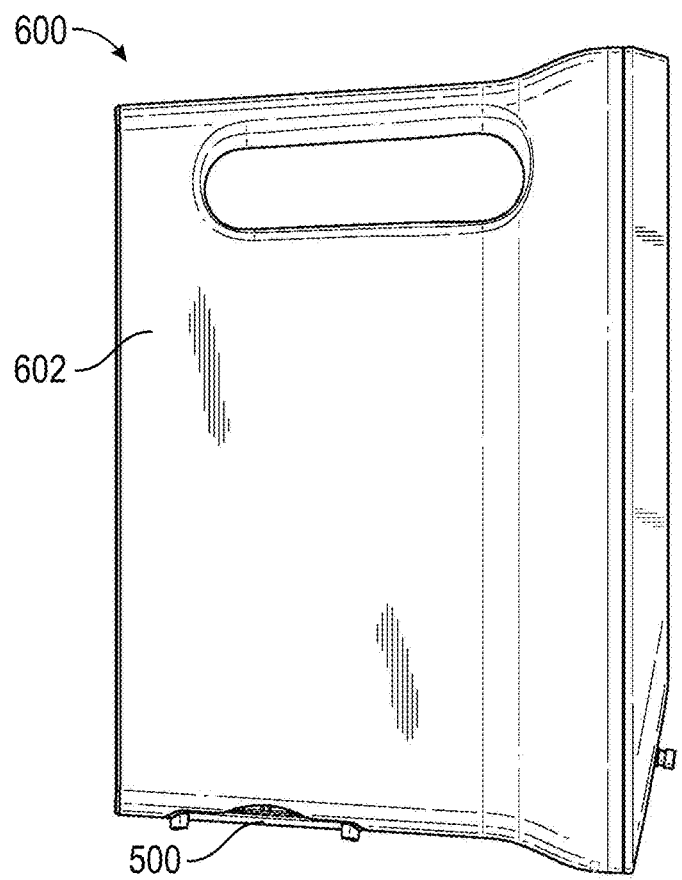
Figure 7C:
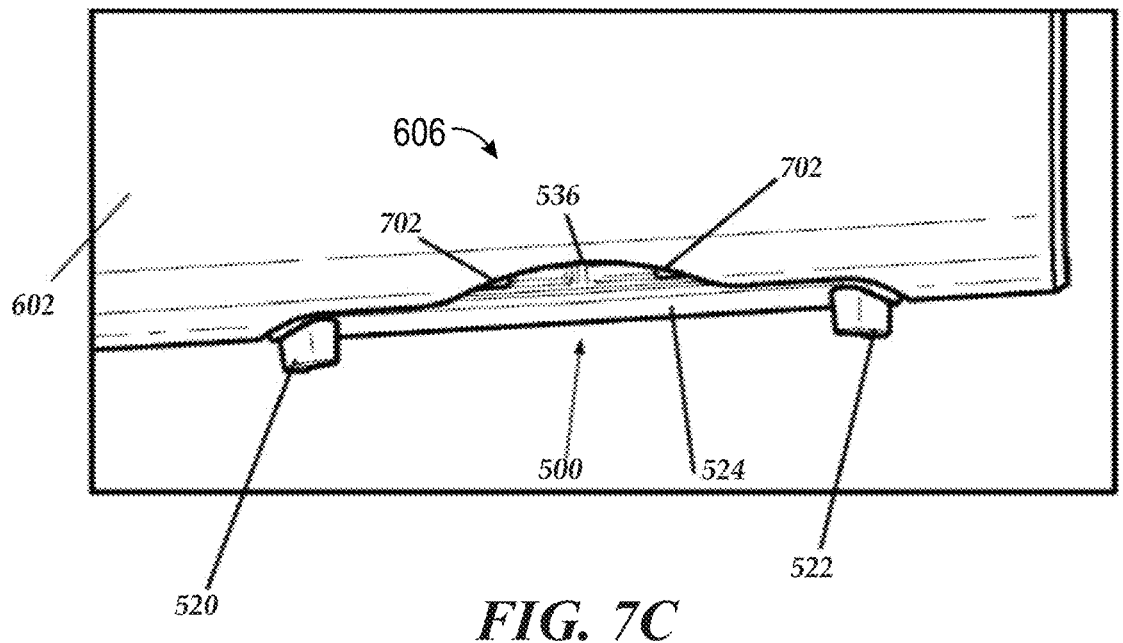

FIGS. 7A-7C illustrate an example patient monitoring device configured in a first configuration, according to some embodiments. The vent cover 500 is configured to protect one or more air vents (for example, vents 802 of FIG. 8A) from external contaminants without occluding (or only partially occluding) the air vents. Accordingly, the vent cover 500 can protect the patient monitoring device from contaminants while also permitting cooling/exhaust, for example, through the air vents. As described herein, the housing 602 includes section 606 which can be one or more depressions, slots, notches or other indentations in the housing 602. The section 606 can be sized to fit the vent cover 500. For example, the section 606 can be the approximately the same shape as (for example, slightly larger than) the body 524 of the vent cover 500 such that the vent cover 500 can fit within the section 606. The vent cover can protect one or more vents of the patient monitor from external contaminants.

FIG. 7A illustrates a bottom view of the housing 602 coupled to the vent cover 500 while the vent cover is in a first configuration. While in the first configuration, the patient monitor is in a more compact state as compared to the second configuration. For example, indentations 630 can be sized to fit the vent cover 500, and, when in a first configuration, the vent cover 500 can fit at least partially within indentations 630 such that an outer surface of the vent cover is at least partially flush, level, or even with an outer surface of the housing 602.

FIG. 7B illustrates a side view of a patient monitoring device 100 while the vent cover 500 is in a first configuration, according to some embodiments, and FIG. 7C illustrates a detail view of the recess 606 of the side view of FIG. 7B. As illustrated in FIG. 7C, the vent cover 500 can be substantially flush, level, or even with the outer surface of the housing 602. As such, the first configuration advantageously provides a sleek design with a continuous outer surface that is easy to clean and reduces crevices or surfaces that are difficult to clean. In addition, the sleek configuration permits a user to easily carry or store the patient monitoring device (for instance, using carrying handle 164) without having to continuously avoid or worry about catching or snagging the vent cover on a passing object.

When in the first configuration, the vent cover 500 can at least partially cover the one or more ventilation openings, such as ventilation openings 802 of FIG. 8A. However, because of the shape of the vent cover 500 and/or the section 606, a ventilation hole 702 remains un-occluded (or is only partially occluded), such that air can continue to be vented into or out of the patient monitoring device 100. For example, the ventilation hole 702 can provide a passageway into the patient monitoring device and thereby can act as a ventilation hole, despite the fact that the vent cover 500 is occluding ventilation opening 802.

Second Configuration

Figure 8B:
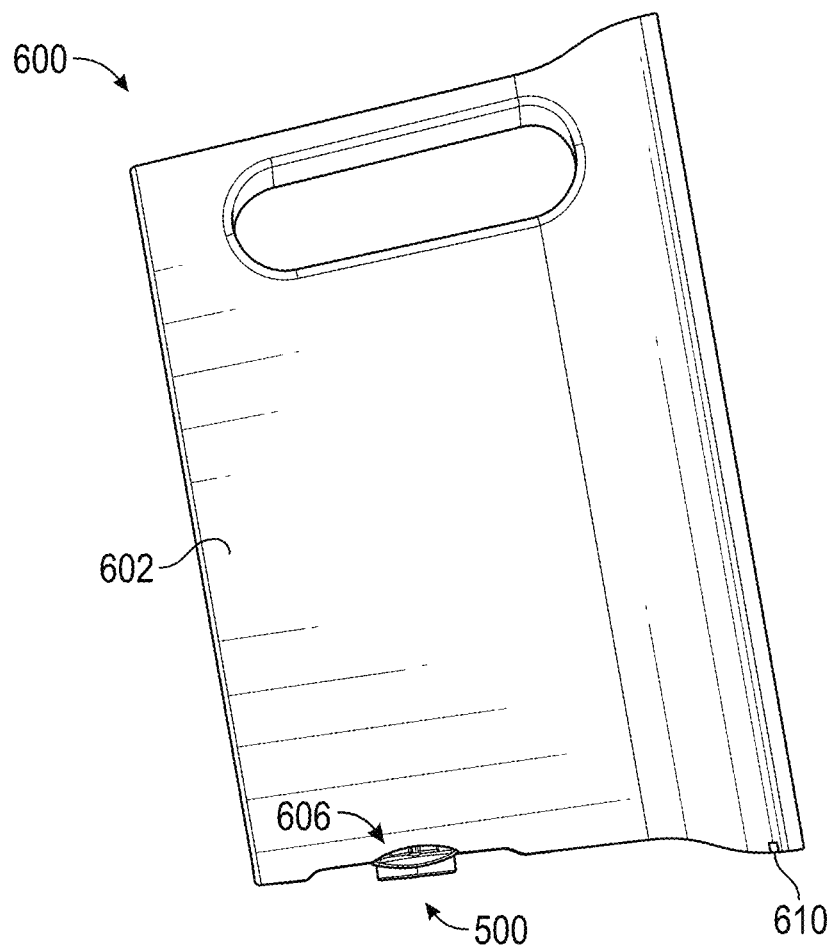
Figure 8C:
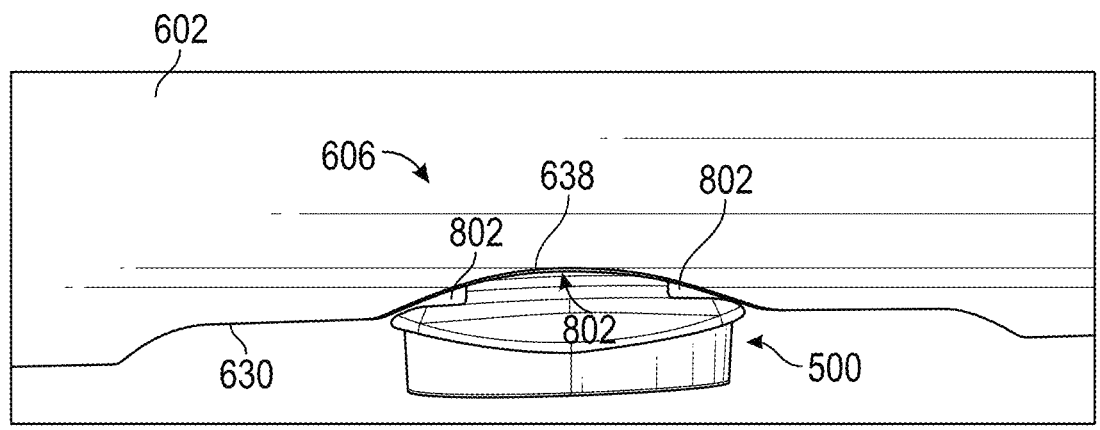

FIGS. 8A-8C illustrate an example patient monitoring device configured in a second configuration, according to some embodiments. FIG. 8A illustrates a perspective view of the patient monitoring device 100. The second configuration of the vent cover 500 can be utilized to provide support to the patient monitoring device 100. For example, the vent cover 500 can be configured to provide a stabilization feature to the patient monitoring device 100 that can keep the patient monitoring device upright.

While in the second configuration, the vent cover 500 and/or the protrusion 610 are configured to aid in supporting the patient monitoring device 100 while it is in an upright position. For example, the protrusion 118 can support the front of the patient monitoring device and/or the vent cover 500 can support the rear of the patient monitoring device. During the second configuration, the vent cover 500 is oriented such that its ends protrude past edges of the housing 602 and provide lateral support to the patient monitoring device 100. The lateral support can limit wobbling and aid in keeping the patient monitoring device 100 in an upright position.

In a second configuration, the vent cover 500 can be oriented (for example, by rotation) such that it is substantially perpendicular to an axis corresponding to the length of the patient monitoring device. The length of the vent cover 500 can vary across embodiments. For example, the vent cover 500 can be longer (for example, 1.5, 2, 2.5, or 3 times longer) than the width of the side of the housing 602. Alternatively, the vent cover 500 can be approximately the same length or is shorter than the width of the side of the housing 602.

The vent cover 500 can provide support to the entire patient monitoring device or can support only a portion of the patient monitoring device. For example, the vent cover 500 can be distal a front portion of the patient monitoring device such that, when in a second configuration, it can support a back end of the patient monitoring device.

FIG. 8B illustrates a side view of the patient monitoring device 100, and FIG. 8C illustrates a detail view of section 606 of FIG. 8B. As shown, the section 606 is defined by the plurality of indentations 630, 632. The curved indentation 638 is shaped such that one or more ventilation holes 802 exist between the housing 602 and the vent cover 500. The ventilation hole 802 provides a passageway into the interior of the housing 602 such that air can flow into or out of the patient monitoring device. Accordingly, the ventilation hole 802 advantageously acts as a ventilation opening, thereby providing additional cooling capabilities to the patient monitor.

Transitioning Between Configurations

The vent cover 500 can be rotated to transition from one configuration (for example, first configuration) to another configuration (for example, second configuration). The configurations may be separated by 45°, 90°, 180° or another angle, and the user can rotate the vent cover 500 about the extension member 538. For example, the extension member 538 can be positioned in the hole 616 of the patient monitor. In some cases, during the transition between a first configuration and a second configuration, the vent cover 500 is in an intermediate configuration, which can be somewhere between first and second configurations. The intermediate configuration can be merely the configuration of the vent cover 500 while it is transitioning from either the second configuration to the first configuration or the first configuration to the second configuration. Alternatively, the intermediate configuration can provide some or all of the functionality of the second configuration and/or the first configuration.

While in the first configuration, the vent cover 500 can be difficult to grab because the vent cover 500 can be positioned within the section 606. Accordingly, to increase the ease of transitioning the vent cover 500 between configurations, the section 606 of the housing 602 may include one or more indentations around the vent cover 500, such as indentations 630. By providing a notch or indentation (such as indentations 630 or 638) in the housing 602, a user can more easily grab the sides of the vent cover 500 and rotate to a new configuration. For example, Indentations 630 and 638 can function as finger slots that permit a user to grasp the body of the vent cover 500. For example, indentations 630 or 638 can recess into the housing such that one or more edges of the vent cover 500 are visible and/or accessible when the vent cover is in the first configuration and/or the second configuration.

The vent cover 500 and/or the housing 602 can include a locking feature which can function to reduce or prevent rotational movement of the vent cover 500. For example, the locking feature can include one or more of raised indentations 642. For instance, the raised indentations 642 may provide some resistance to initial rotation of the vent cover 500. The shape of the extension member 538 and/or the shape of the hole 616 can additional or alternatively function as the locking feature. For example, a locking mechanism can be activated (for example, locked) while the vent cover 500 is in a stabilization configuration such that the vent cover 500 cannot be incidentally rotated or re-positioned. In some instances, a locking feature can provide extra stability to the vent cover 500 or housing 602, for instance, while the vent cover 500 is supporting the patient monitoring device. The locking feature can also or alternatively be engaged when the vent cover 500 is in a first configuration. In some cases, the locking feature can be deactivate or unlocked while the vent cover 500 is changing configurations, such as when the vent cover 500 is in an intermediate configuration.

The vent cover 500 can transition between configurations while coupled to the patient monitoring device 100. For example, the vent cover 500 can be rotated, twisted or swiveled to transition between configurations. The vent cover 500 can be rotated about an axis of the extension member 538. The extension member axis can be approximately perpendicular to the body 524 of the vent cover 500. One or more configurations can be separated by approximately 45, 90, 135, or 180 degrees of rotation of the vent cover 500. For example, if the vent cover 500 is configured in a first configuration, then the vent cover 500 will transition into a second configuration upon rotation of the vent cover approximately 90°. The vent cover 500 can transition between configurations through a clockwise or counter-clockwise rotation. Alternatively, the vent cover 500 can be permitted only to rotate in a single direction. In some cases, the vent cover 500 can be at least partially rotationally symmetric. That is, the configuration of the vent cover 500 will be in the same if rotated in either direction approximately 180°.

Although described herein as a vent cover, in some cases the vent cover 500 may not cover a ventilation hole. Rather, the vent cover 500 (sometimes referred to as a swivel foot) can be configured to function as a stabilizing feature. For example, as described herein, the swivel foot 500 can be swivelable (for example, when rotated by a user) and can be swiveled between various configurations. In a first configuration, the swivel foot 500 can be swiveled parallel to a lengthwise axis of the device. In the first configuration, the swivel foot 500 can fit within indentions of a recess defined by the housing of the patient monitoring device such that an outer surface of the swivel foot 500 is at least partially flush, level, or even with an outer surface of the housing. This maintains the sleek, smooth design of the patient monitoring device, making it easier to clean and more portable. The first configuration can be useful when moving or storing the patient monitoring device, or when the patient monitoring device is operating in a landscape mode for example. In a second configuration, the swivel foot 500 can be swiveled perpendicular to the first configuration and perpendicular to a lengthwise axis of the device. The second configuration can provide support and stability to the patient monitoring device. For example, the swivel foot 500 can aid in stabilizing the patient monitoring device, particularly when the device is in a portrait mode and is less stable.

Smooth and Easy to Clean Design

The disclosure advantageously provides for a patient monitoring device which is sleeker and easier to clean than conventional patient monitoring devices that have many crevices and holes. Specifically, the patient monitoring devices disclosed herein can include a housing configured to connect together and to house a display using a limited number of screws while still allowing the devices to be serviceable. By limiting a number of screw holes or other holes or crevices, the housing can have fewer crevices, which can reduce the amount of dirt or other contaminants that are stuck in the housing.

Figure 9:
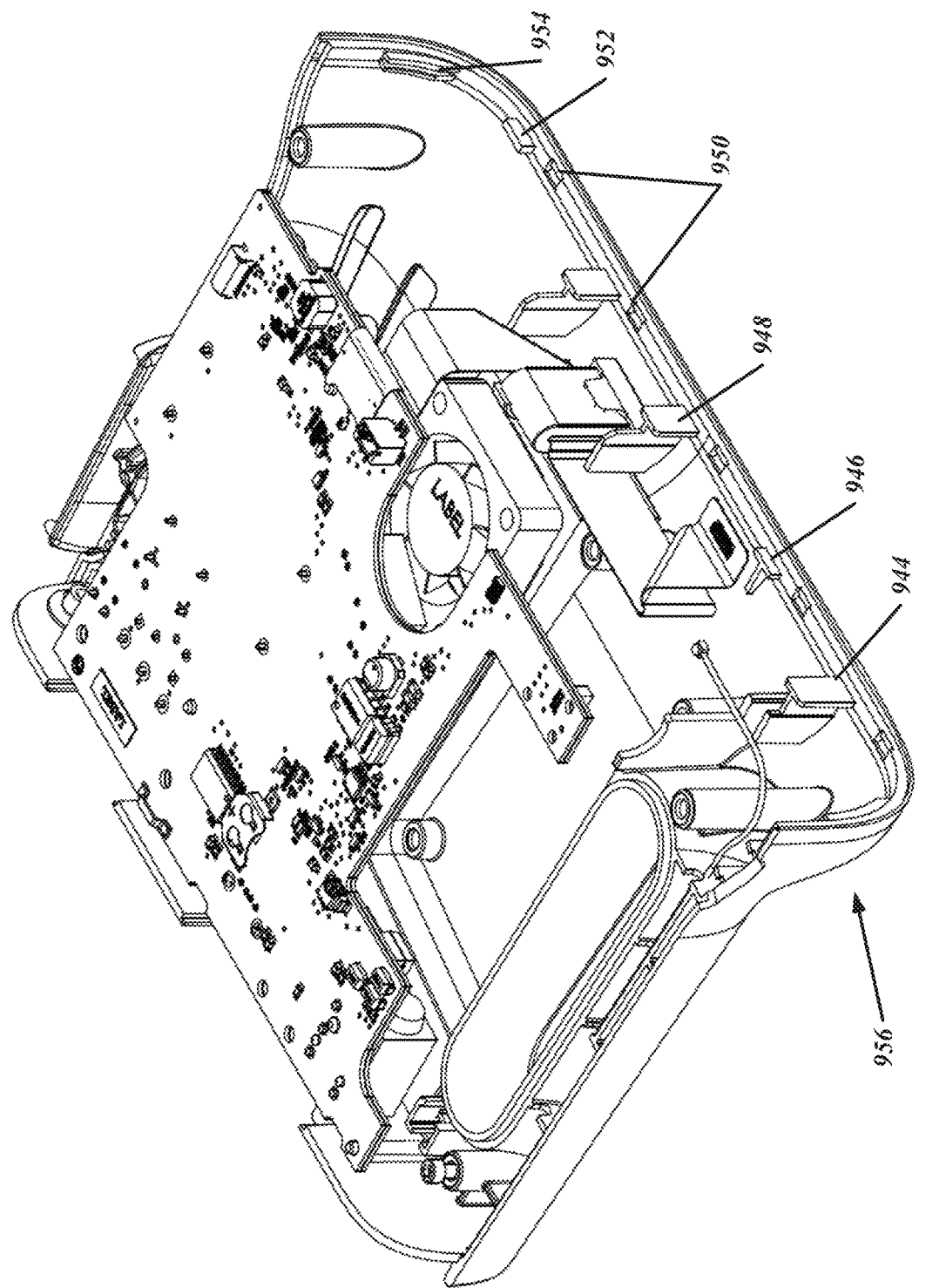
FIGS. 9-10 illustrate example internal structural components of a patient monitoring device.
Figure 10:
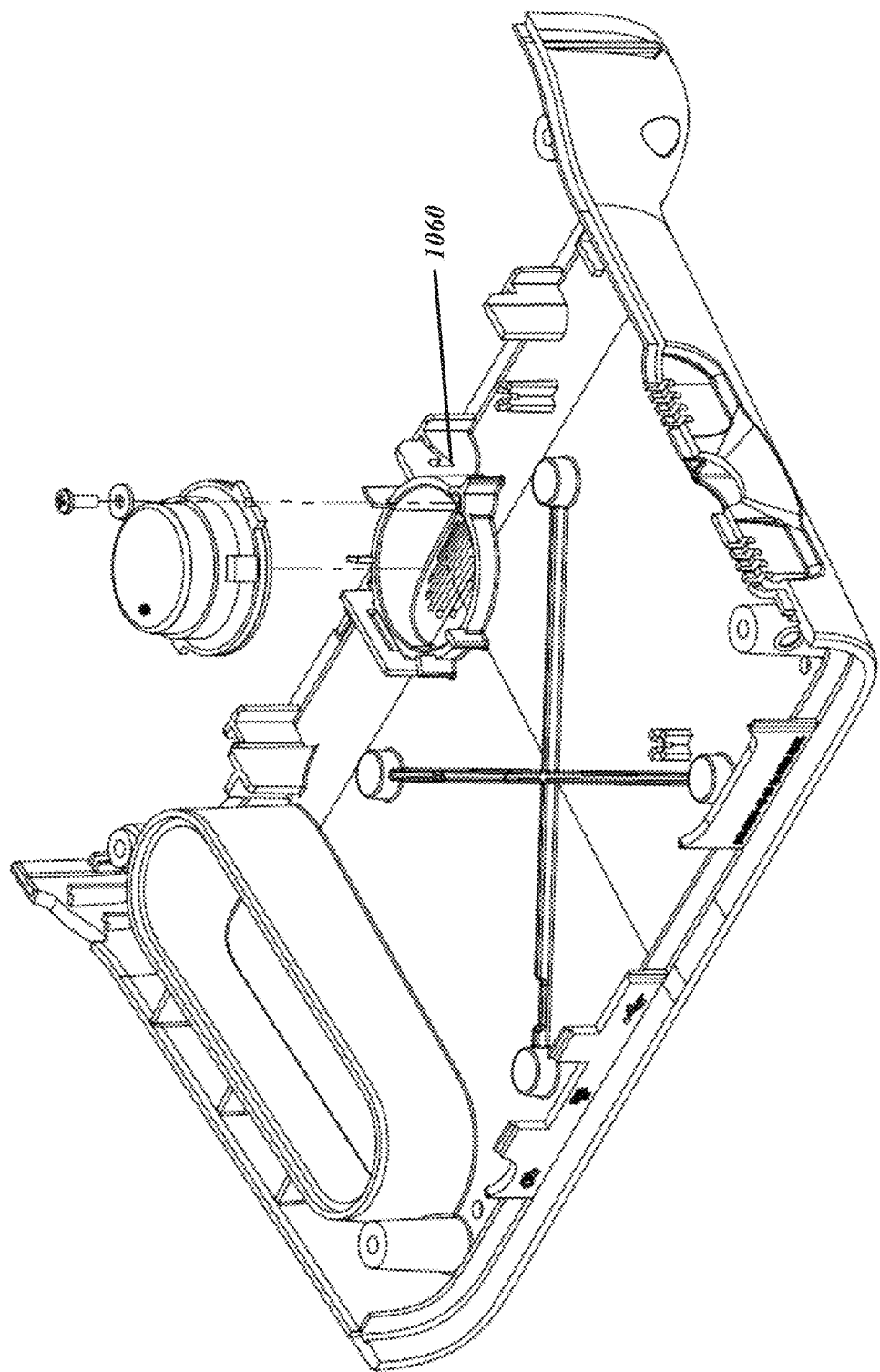
Figure 11C:
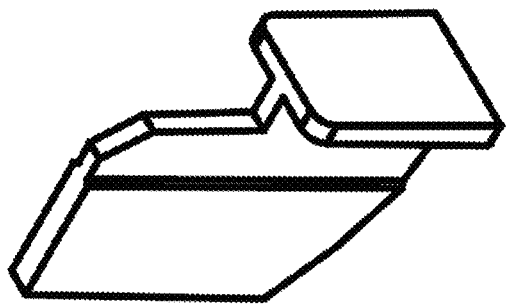
FIGS. 11A-11F illustrate a plurality of example connection features for coupling portions of a housing of a patient monitor.
Figure 11F:
Figure 11B:
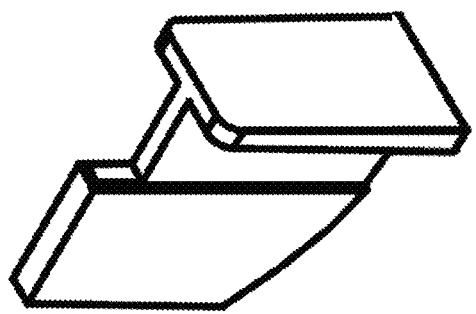
Figure 11E:
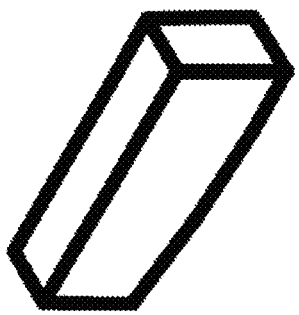
Figure 11A:
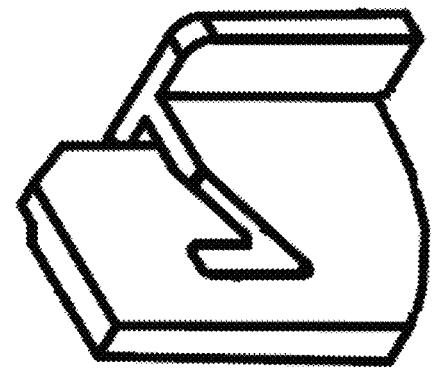
Figure 11D:
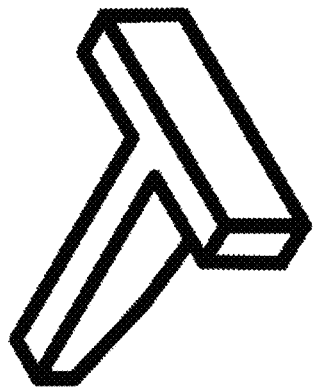

FIGS. 9-10 illustrate example internal structural components of a patient monitoring device. In some instances, the shape or location of a connection feature can be dependent on its position, function, etc. within the patient monitoring device. For example, the connection feature can include a simple t-shaped design that can fit in a corresponding t-shaped hole, functioning similar to a lock and key. Alternatively, the connection feature can include a peg 952 or other insert 954 which can connect to a corresponding hole. The connection feature can be tall, such as connection features 944, 948, which can, for example, provide structural support within the patient monitor. In some instances, the connection feature can be beveled or include a slot (such as connection feature 1060 of FIG. 10) to, for instance, provide a slot for a cable.

FIGS. 11A-11F illustrate a plurality of example connection features which can be utilized to connect portions of housing together, thus obviating or reducing the number of screws required for connecting the housing portions. As illustrated in FIG. 12, which is described in more detail below, each of the connection portions can have corresponding connection portions that mate together, for example, by inserting one into the other or snapping together. It should be noted that while FIGS. 11A-11F illustrated a plurality of connections features, this is not intended to illustrate an exhaustive list. For example, a connection feature can include a lock and key or one more elements that can be twisted to hold the chassis/housing together. One or more additional features can be utilized to connect the portions of the housing together, such as connecting the display housing to a side portion of the housing.

Figure 12A:
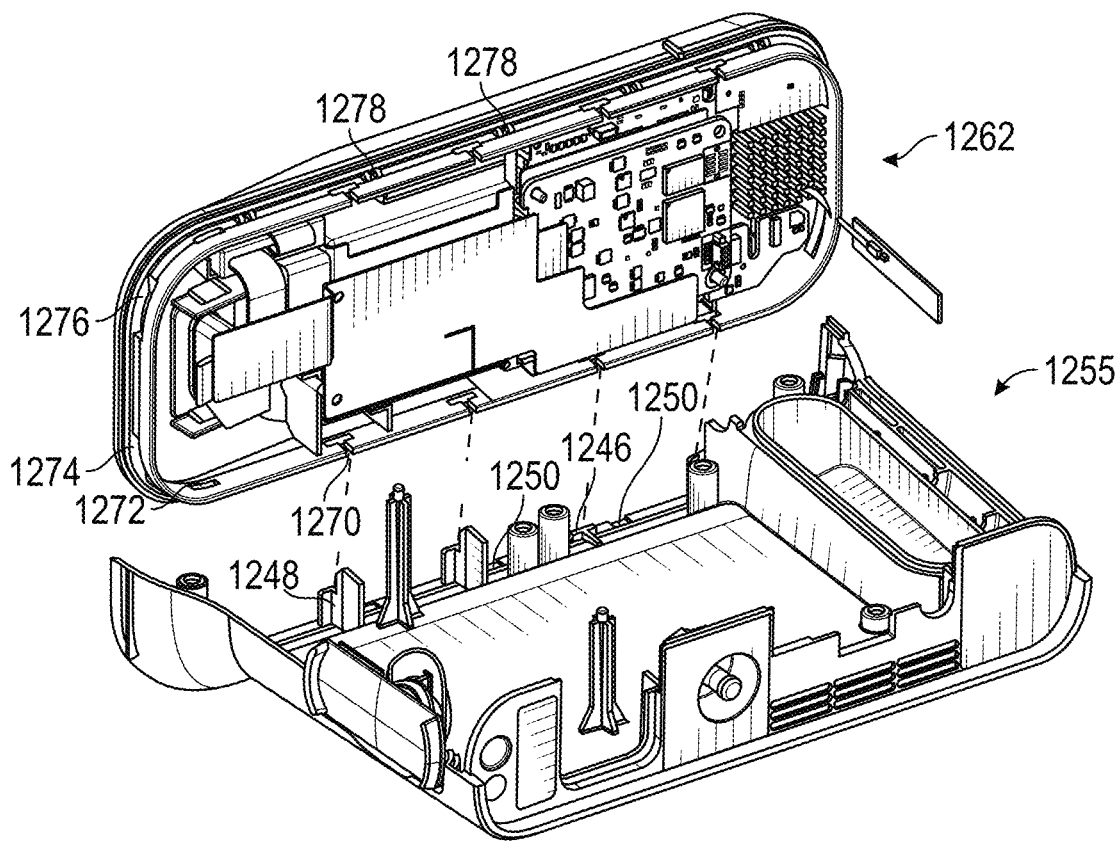
FIGS. 12A-12B illustrate example connections between a display housing and a side housing.
Figure 12B:
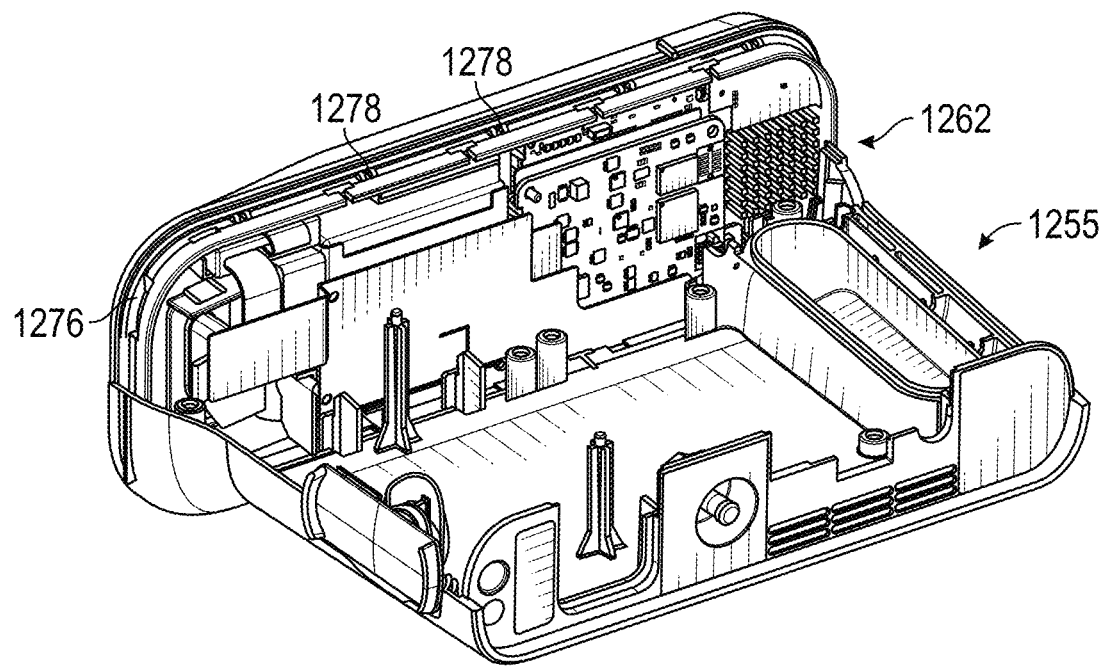

FIGS. 12A-12B illustrate example connections between a display housing 1262 and a first side housing 1255. The first side housing 1255 includes a plurality of connection features, such as connection features 1246, 1248, and 1250. Similarly, the display housing 1262 includes a plurality of corresponding connection features, such as connection features 1270, 1272, 1274, and 1278.

As shown by the dashed lines in FIG. 12A, the display housing 1262 can be connected to the first side housing 1255 via the mating of a plurality of connection features. For example, connection feature 1270 (an aperture) can be aligned with connection feature 1248 (an insert). Similarly, connection features 952, 954 (inserts), as illustrated in FIG. 9, can be aligned with connection features 1272, 1274 (apertures), respectively. In addition, connection features 1278 (insert) can be inserted or snapped into connection features 1250 (slots). The display housing 1262 can be also connected to a second side housing in the same or similar manner. As shown, the mating arrangements of the housing portions allow the front housing 1262 to be held in place securely without using screws (or, in some cases, only using a limited number of screws), which reduces the number of crevices that must be cleaned.

Figure 13A:
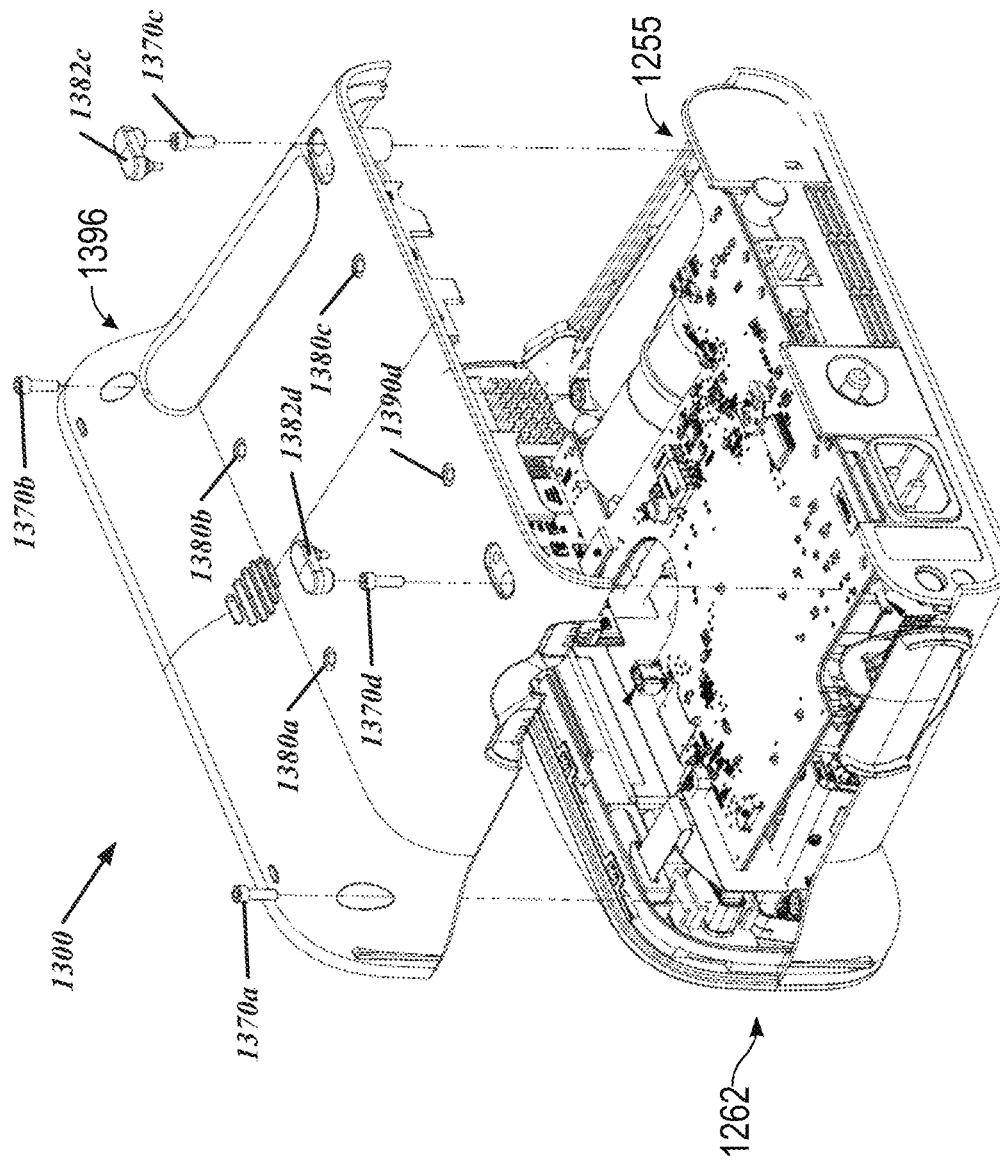
FIG. 13A illustrates an exploded view of an example patient monitoring device.

FIG. 13A illustrates example connections between a second side housing 1396, the display housing 1262, and the first side housing 1255. As described herein, the display can connect to the side housings 1396, 1255 without using screws, or only using a limited number of screws, which reduces the number of crevices that must be cleaned. Similarly, the side housings 1396, 1255 can connect using no or a limited number of screws. In some cases, the screws connecting the side housing can further secure the display housing within the patient monitoring device. In this example, the first side housing 1255 and the second side housing 1396 are connected using four screws 1370*a*, 1370*b*, 1370*c*, and 1370*d* are utilized. However, various other numbers of screws can be used.

In some cases, the housing can include a plurality of connection points 1280*a*, 1280*b*, 1280*c*, and/or 1280*d* for mounting the patient monitoring device 1300, such as to a cart or wall. When the patient monitoring device 1300 is not mounted, one or more plugs can be inserted into the connection points 1380*a*, 1380*b*, 1380*c*, and/or 1380*d* to reduce the number of open crevices. Similarly, one or more plugs, such as plug 1282*c* or 1282*d*, can be inserted into the screw holes to further reduce the number of open crevices.

Figure 13B:
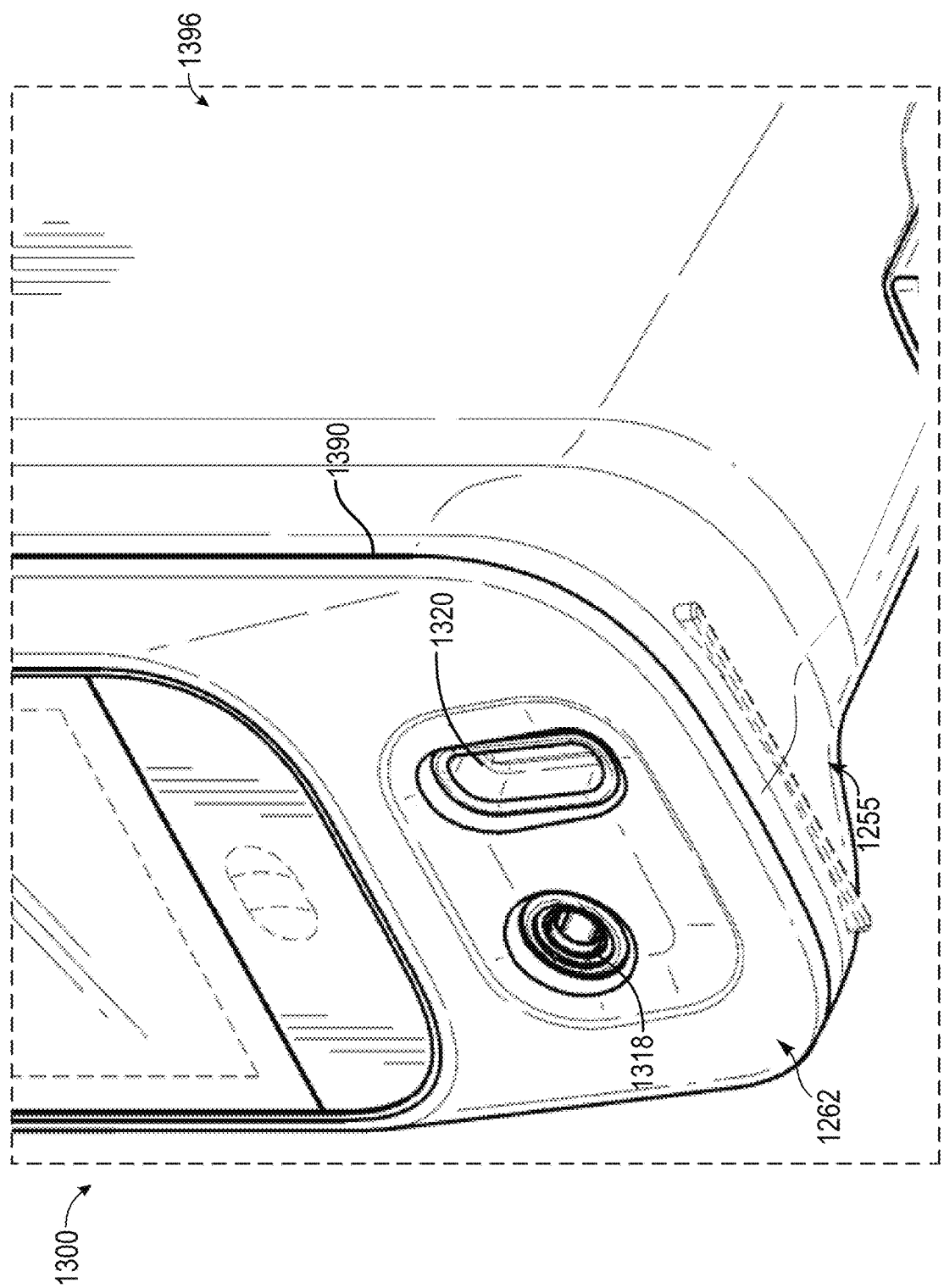
FIG. 13B illustrates a detail view of the seam between the various housing portions of FIG. 13A.

FIG. 13B illustrates a detailed view of the seam 1390 or connection between the housing portions. As illustrated, when the front housing 1262, the first side housing 1255, and the second side housing 1396 are connected together, a tight seam 1390 exists between the housing portions to maintain to sleek and limited crevice design of the patient monitoring device 1300. In addition, the front portion of the patient monitoring device 1300 advantageously has few or no indentations, for example, with the exception of ports 1318 and 1390. In many instances, during use, the display faces the patient. As a result, the screen and the periphery of the screen are likely to collect or accumulate patient fluids. By reducing or limiting an amount of crevices of the patient monitoring device, especially the front portion and periphery of the front portion, fluids from the patient (or other fluids) cannot or are less likely to enter or be stuck in or on the patient monitoring device.

Flow Diagrams

Figure 14:
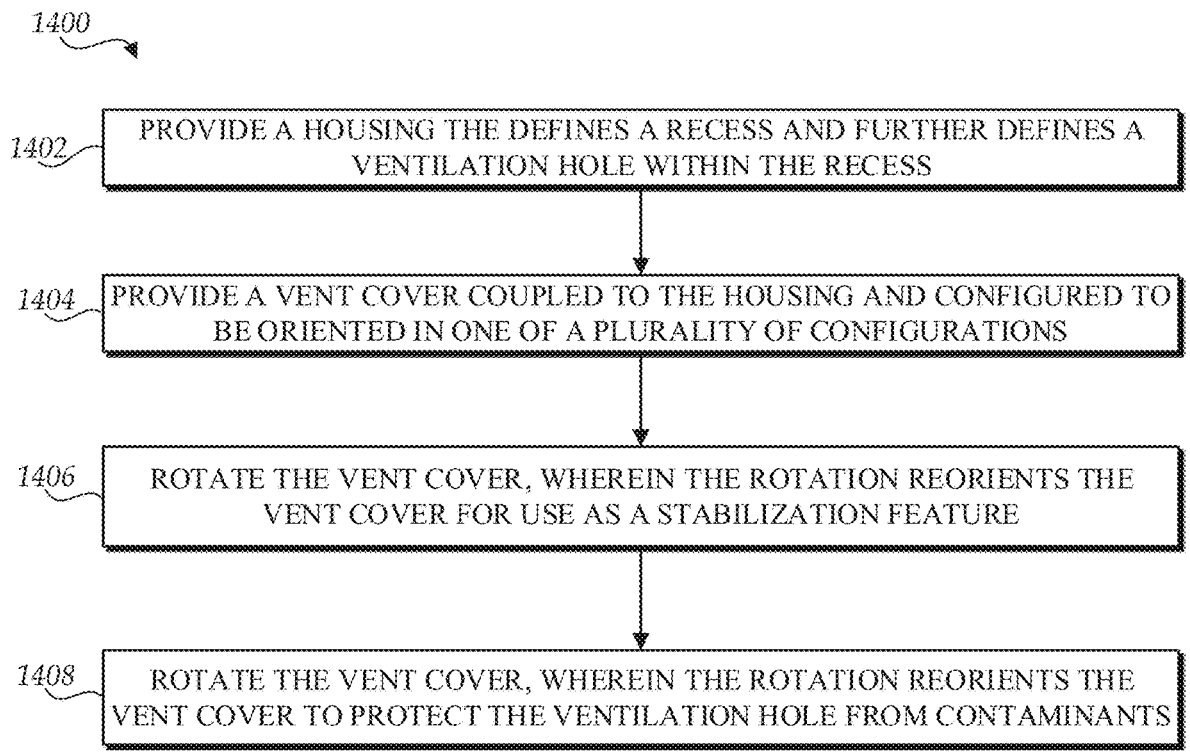
FIG. 14 is a flow diagram illustrative of an example of a routine for reconfiguring a vent cover.

FIG. 14 is a flow diagram illustrative of an example of a routine for reconfiguring a vent cover. One skilled in the relevant art will appreciate that the various blocks described herein with reference to FIG. 14 can be implemented in a variety of orders. For example, a user can implement some blocks concurrently or change the order as desired. Furthermore, it will be understood that fewer, more, or different blocks can be used as part of the routine 1400.

At blocks 1402 and 1404, a patient monitoring device and a vent cover are provided. The vent cover and patient monitoring device can include any of the features as described herein. For example, the housing can define a recess and can further define one or more ventilation holes in the recess. The vent cover can be coupled to the housing, such as at the recess. For example, when coupled together, the vent cover can reside within or partially within the recess. The patient monitoring device and vent cover can be provided as one unit or can be provided separately. For example, where the patient monitoring device and vent cover are provided separately (for example, not attached), the routine 1400 can further include coupling the vent cover to the patient monitoring device. The coupling can include inserting the vent cover into the hole 616 of the patient monitoring device. In some cases, coupling can further include flexing the wings of the engagement member, inserting the engagement member into a hole of the patient monitoring device, and/or un-flexing the wings of the engagement member.

At block 1406, the vent cover can be rotated (for example, by a user) to the second configuration. As described herein, in the second configuration, the vent cover can be act as a stand or other stabilizing feature for the patient monitoring device. For example, the vent cover can be swiveled or rotated perpendicular to the first configuration and perpendicular to a lengthwise axis of the device. While in the second configuration, the vent cover can provide support and stability to the patient monitoring device. For example, the vent cover can aid in stabilizing the patient monitoring device, particularly when the device is in a portrait mode and is less stable. In this second configuration, the vent cover can be configured such that it does not prevent a flow of air through the ventilation hole.

At block 1408, the vent cover can be rotated (for example, by a user) to the first configuration. As described herein, in the first configuration, the vent cover can protect the ventilation hole(s) from external contaminants, while still allowing air to vent the ventilation hole. For example, the patient monitor may be positioned proximate the patient such that patient fluids or other substances are likely to come in contact with the patient monitor. The vent cover can shield the ventilation hole to keep these substances from entering the patient monitor through the ventilation hole. In the first configuration, the vent cover can be swiveled parallel to a lengthwise axis of the device. In addition or alternatively, the vent cover can fit within indentions of a recess defined by the housing of the patient monitoring device such that an outer surface of the vent cover is at least partially flush, level, or even with an outer surface of the housing. This maintains the sleek, smooth design of the patient monitoring device, making it easier to clean and more portable. The first configuration is useful when moving or storing the patient monitoring device, or when the patient monitoring device is operating in a landscape mode for example. In this first configuration, the vent cover can be configured such that it does not prevent a flow of air through the ventilation hole.

Throughout the process 1400, the vent cover can be configured such that it does not prevent a flow of air through the ventilation hole. Accordingly, process 1400 demonstrates the multipurpose advantage of the vent cover in that is can provide both a shielding configuration (for example, via the first configuration) and/or a supporting or stabilizing configuration (for example, via the second configuration).

Depending on the embodiment, certain acts, events, or blocks, identified in process 1400 can be performed in a different sequence, can be added, merged, or left out altogether (non-limiting example: not all described blocks are necessary). For example, any one of blocks 1406 or 1408 can be omitted. Moreover, block 1408 can be performed prior to block 1408, Furthermore, in some cases, the patient monitor may not include and/or the vent cover may not cover a ventilation hole. Rather, in the first configuration, the vent cover (which, in this example is sometimes referred to as a swivel foot) can simply be configured to be oriented parallel to a lengthwise axis of the device and fit within indentions of a recess defined by the housing of the device. Further, an outer surface of the swivel foot can be at least partially flush, level, or even with an outer surface of the housing. This maintains the sleek, smooth design of the patient monitoring device, making it easier to clean and more portable. The first configuration can be useful when moving or storing the patient monitoring device, or when the patient monitoring device is operating in a landscape mode for example. However, as described above, the swivel foot may or may not be protecting a ventilation hole. The second configuration of the swivel foot can correspond to the second configuration as described herein. For example, the swivel foot can be swiveled between perpendicular to the first configuration and perpendicular to a lengthwise axis of the device. The second configuration can provide support and stability to the patient monitoring device. For example, the swivel foot can aid in stabilizing the patient monitoring device, particularly when the device is in a portrait mode and is less stable.

Terminology

The term "and/or" herein has its broadest least limiting meaning which is the disclosure includes A alone, B alone, both A and B together, or A or B alternatively, but does not require both A and B or require one of A or one of B. As used herein, the phrase "at least one of" A, B, "and" C should be construed to mean a logical A or B or C, using a non-exclusive logical or.

The following description is merely illustrative in nature and is in no way intended to limit the disclosure, its application, or uses. For purposes of clarity, the same reference numbers may be used in the drawings to identify similar elements. It should be understood that steps within a method may be executed in different order without altering the principles of the present disclosure.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

The term "plethysmograph" includes it ordinary broad meaning known in the art which includes data responsive to changes in volume within an organ or whole body (usually resulting from fluctuations in the amount of blood or air it contains).

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable components that provide the described functionality; or a combination of some or all of the above, such as in a system-on-chip. The term module may include memory (shared, dedicated, or group) that stores code executed by the processor.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage. Although the foregoing invention has been described in terms of certain embodiments, other embodiments will be apparent to those of ordinary skill in the art from the disclosure herein. Additionally, other combinations, omissions, substitutions and modifications will be apparent to the skilled artisan in view of the disclosure herein. Accordingly, the present invention is not intended to be limited by the reaction of the preferred embodiments, but is to be defined by reference to claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. A patient monitoring device configured to communicate with one or more physiological sensors and determine at least one physiological parameter of a patient, comprising: a sensor input configured to receive communications from a physiological sensor coupled to a patient; a housing configured to house a display, wherein the housing defines a recess and further defines one or more ventilation holes within the recess, wherein the one or more ventilation holes allow air to flow through the housing of the patient monitoring device, while the device is in use, the display is configured to display in a portrait mode when the patient monitoring device is in an upright orientation or a landscape mode when the patient monitoring device is in a landscape orientation; and a vent cover coupled to the housing and configured to be positioned in one of a plurality of configurations comprising at least: a first configuration wherein the vent cover is oriented within the recess to at least partially cover the one or more ventilation holes to protect the one or more ventilation holes from at least some external contaminants, wherein the covering of the one or more ventilation holes by the vent cover continues to permit the air to flow through the housing of the patient monitoring device through the one or more ventilation holes, and a second configuration wherein the vent cover is oriented to provide a stabilization feature to the patient monitoring device and aid in keeping the patient monitoring device in the upright position, wherein the orientation of the vent cover in the second configuration does not cover the one or more ventilation holes, wherein rotation of the vent cover transitions the vent cover between the first configuration and the second configuration.

2. The patient monitoring device of claim 1, wherein the first configuration further comprises at least a portion of an outer surface of the vent cover being level with at least a portion of an outer surface of the housing.

3. The patient monitoring device of claim 1, wherein the recess includes first indentations and second indentations, wherein the vent cover resides in the first indentations in the first configuration and the vent cover resides in the second indentations in the second configuration.

4. The patient monitoring device of claim 3, wherein the first indentations are perpendicular to the second indentations.

5. The patient monitoring device of claim 3, wherein the housing further defines one or more raised indentations to provide a barrier between the first indentations and the second indentations.

6. The patient monitoring device of claim 1, wherein the stabilization feature provides lateral support to the patient monitoring device.

7. The patient monitoring device of claim 1, further comprising a locking mechanism configured to limit rotation of the vent cover.

8. The patient monitoring device of claim 7, wherein the stabilization feature includes the vent cover oriented such that its ends protrude past edges of the housing.

9. The patient monitoring device of claim 1, wherein the vent cover includes a body, an engagement member, and an extension member, the extension member extending between the body and the engagement member.

10. The patient monitoring device of claim 9, wherein the vent cover is configured to rotate about an axis corresponding to the extension member.

11. The patient monitoring device of claim 1, wherein the first configuration and the second configuration are separated by 90 degrees of rotation of the vent cover.

12. The patient monitoring device of claim 1, wherein the housing is configured to house at least one of a non-invasive blood pressure module, a capnography module, or a pulse oximetry module.

13. The patient monitoring device of claim 1, wherein the housing comprises a plurality of housing portions configured to mate via a plurality of connection features to attach the housing portions together, wherein the plurality of connection features comprise one or more of t-shaped connection features and/or snap connection features.

14. The patient monitoring device of claim 13, wherein the t-shaped connection features comprise a t-shaped protrusion and a t-shaped aperture configured to mate with the t-shaped protrusion.

* * * * *